United States Patent
Schuck et al.

(10) Patent No.: US 11,974,966 B2
(45) Date of Patent: *May 7, 2024

(54) MEDICAL PRODUCT INCLUDING PRE-FILLED PRODUCT BAG

(71) Applicants: BAXTER INTERNATIONAL INC., Deerfield, IL (US); BAXTER HEALTHCARE SA, Glattpark (CH)

(72) Inventors: David Filiberto Schuck, Long Grove, IL (US); Karl Hans Cazzini, Lindenhurst, IL (US); Yuanpang Samuel Ding, Long Grove, IL (US); Ying-Cheng Lo, Long Grove, IL (US); Grant Anthony Bomgaars, Kildeer, IL (US); Thomas Edward Dudar, Palatine, IL (US); Mark Edward Pasmore, Grayslake, IL (US); Bernd Krause, Rangendingen (DE); Michael Joseph Sadowski, Ringwood, IL (US); Anastasios Hristakos, Evanston, IL (US); Joseph Vincent Ranalletta, Greenville, SC (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 1148 days.

This patent is subject to a terminal disclaimer.

(21) Appl. No.: 16/631,030

(22) PCT Filed: Jul. 12, 2018

(86) PCT No.: PCT/US2018/041807
§ 371 (c)(1),
(2) Date: Jan. 14, 2020

(87) PCT Pub. No.: WO2019/018200
PCT Pub. Date: Jan. 24, 2019

(65) Prior Publication Data
US 2020/0146932 A1    May 14, 2020

Related U.S. Application Data

(60) Provisional application No. 62/533,408, filed on Jul. 17, 2017.

(51) Int. Cl.
*A61J 1/14* (2023.01)
*A61J 1/10* (2006.01)
(Continued)

(52) U.S. Cl.
CPC .............. *A61J 1/1456* (2015.05); *A61J 1/10* (2013.01); *A61J 1/1475* (2013.01); *A61J 1/2024* (2015.05);
(Continued)

(58) Field of Classification Search
CPC    A61J 1/1456; A61J 1/10; A61J 1/1475; A61J 1/2024; A61J 1/1443; A61J 1/2093;
(Continued)

(56) References Cited

U.S. PATENT DOCUMENTS 3,207,420 A * 9/1965 Navarrete-Kindelan ..................... F25C 1/243
426/414
4,636,313 A * 1/1987 Vaillancourt .......... B01D 63/06
604/326

(Continued)

FOREIGN PATENT DOCUMENTS

EP    0116362 A2    8/1984
JP    2001037847 A *  2/2001    ......... B65D 81/3266
(Continued)

OTHER PUBLICATIONS

International Application No. PCT/US2018/041807, International Search Report and Written Opinion, dated Sep. 25, 2018.
(Continued)

*Primary Examiner* — Ariana Zimbouski
(74) *Attorney, Agent, or Firm* — MARSHALL, GERSTEIN & BORUN LLP

(57) ABSTRACT

A medical product includes a bladder, a filtration device, and a sterile product concentrate. The bladder has a perimeter
(Continued)

seal and defining a sterile chamber. The filtration device includes a stem and a filter membrane disposed in line with the stem. The stem extends through the perimeter seal and has an inlet end accessible from outside of the perimeter seal and an outlet end in fluid communication with the sterile chamber. The filter membrane can have a nominal pore size in a range of approximately 0.1 µm to approximately 0.5 µm, wherein the filter membrane is shaped as a hollow fiber with a wall and pores residing in the wall of the fiber. The sterile product concentrate is disposed in the sterile chamber and adapted to be reconstituted by the introduction of a pharmaceutical fluid into the chamber through the filtration device.

21 Claims, 12 Drawing Sheets

(51) Int. Cl.
  *A61J 1/20* (2006.01)
  *B01D 63/02* (2006.01)
(52) U.S. Cl.
  CPC ........ *A61J 1/2093* (2013.01); *B01D 63/0241* (2022.08)
(58) Field of Classification Search
  CPC ...... A61M 2005/1655; A61M 2205/75; A61M 5/165; B01D 63/024
  See application file for complete search history.

(56) References Cited

U.S. PATENT DOCUMENTS

| | | | |
|---|---|---|---|
| 5,577,369 A | 11/1996 | Becker et al. | |
| 5,681,463 A * | 10/1997 | Shimizu | B01D 61/18 210/282 |
| 5,885,454 A | 3/1999 | Yagihashi et al. | |
| 6,322,044 B1 * | 11/2001 | Vangedal-Nielsen | B31B 70/00 249/119 |
| 7,347,937 B1 | 3/2008 | Cheng et al. | |
| 10,617,603 B2 * | 4/2020 | Bomgaars | A61J 1/1456 |
| 11,318,069 B2 * | 5/2022 | Ding | A61J 1/10 |
| 2006/0045392 A1 * | 3/2006 | Bannister | B65D 33/01 383/102 |
| 2009/0113753 A1 * | 5/2009 | Pepper | A61B 50/13 34/92 |
| 2010/0185171 A1 * | 7/2010 | Muramatsu | B29C 65/1616 604/408 |
| 2020/0146931 A1 * | 5/2020 | Doty | A61J 1/1475 |

FOREIGN PATENT DOCUMENTS

| | | | | |
|---|---|---|---|---|
| JP | 2018144821 A | * | 9/2018 | |
| WO | WO-01/91694 A1 | | 12/2001 | |
| WO | WO-0191694 A1 | * | 12/2001 | ............... A61J 1/10 |
| WO | WO-2016/174749 A1 | | 11/2016 | |

OTHER PUBLICATIONS

International Search Report for International Application No. PCT/US2018/041807, dated Sep. 25, 2018.
Written Opinion for International Application No. PCT/US2018/041807, dated Sep. 25, 2018.
European Patent Application No. 18749220.2, Communication Pursuant to Article 93(3) EPC, dated Sep. 12, 2022.

* cited by examiner

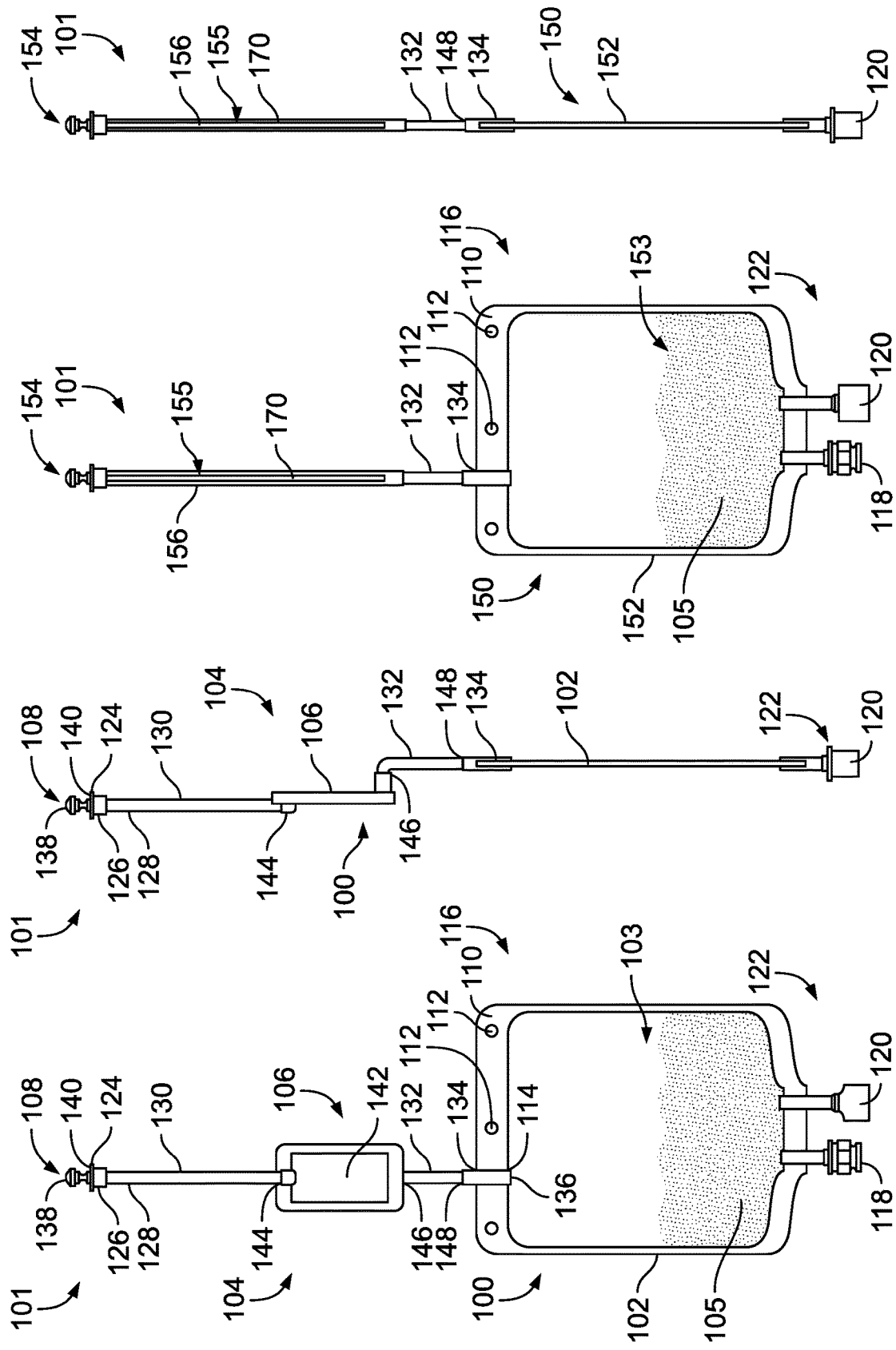

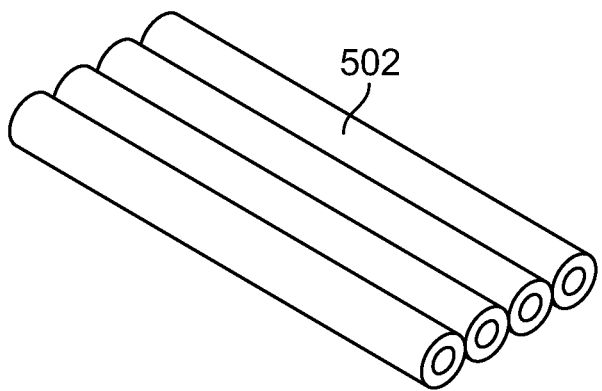
FIG. 13
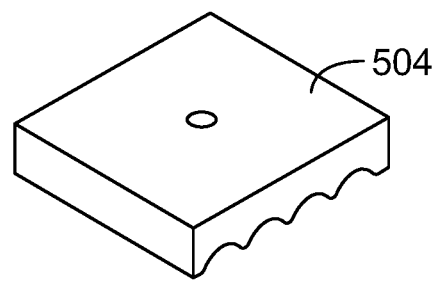
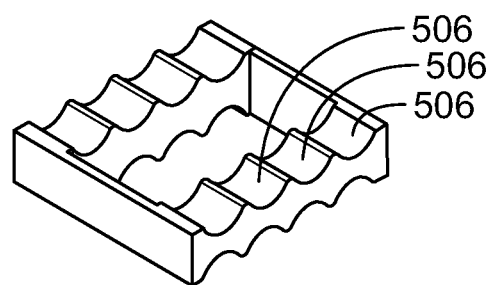
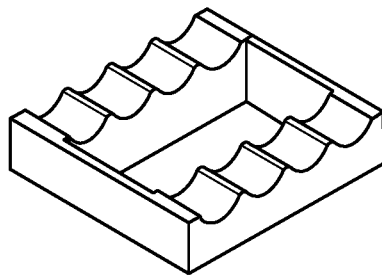
FIG. 14

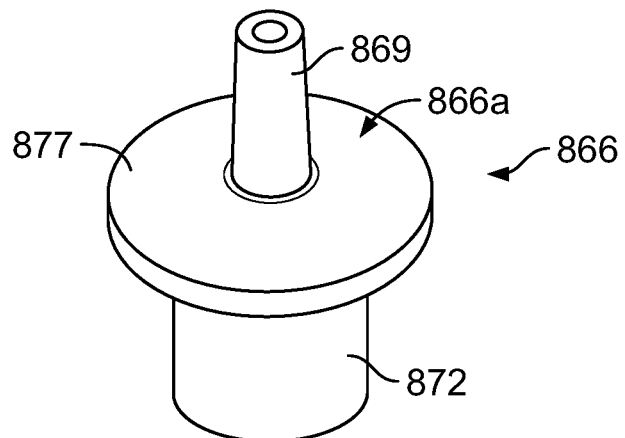
FIG. 16
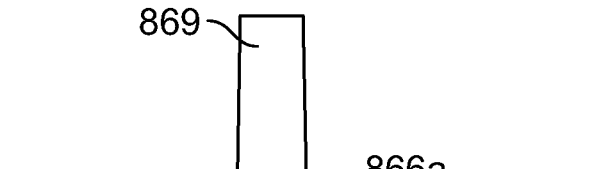
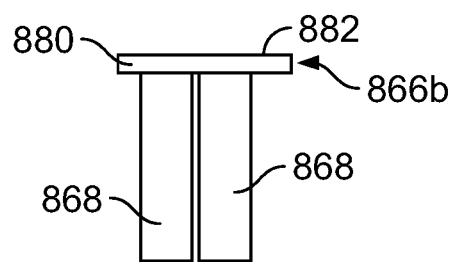
FIG. 17

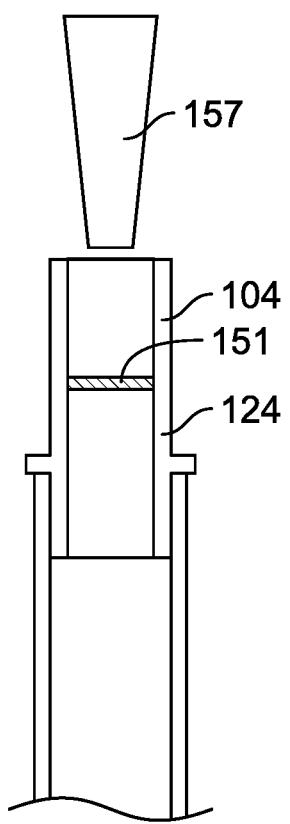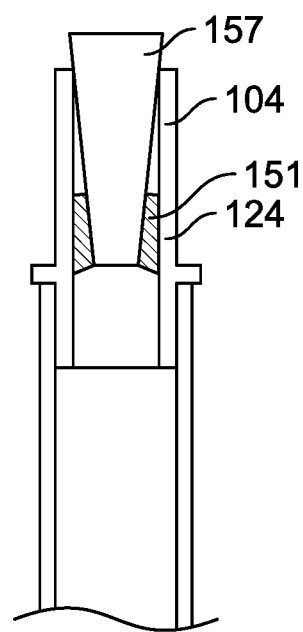
FIG. 21  FIG. 22

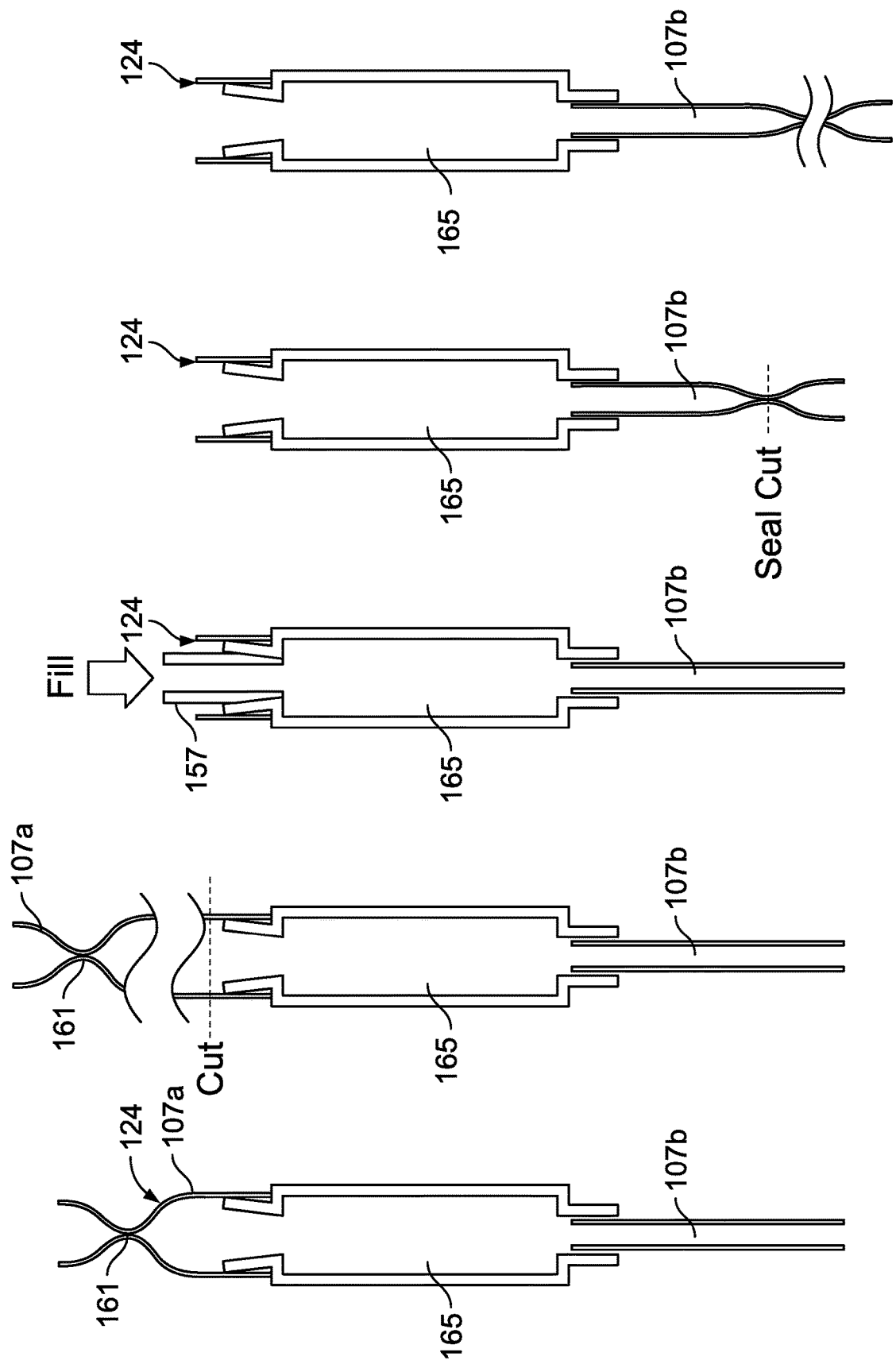

MEDICAL PRODUCT INCLUDING PRE-FILLED PRODUCT BAG

CROSS-REFERENCE TO AND RELATED APPLICATIONS

Priority is claimed to U.S. Provisional Application Ser. No. 62/533,408, filed Jul. 17, 2017, the entire contents of which are incorporated herein by reference.

Additionally, the following related and co-owned applications are hereby expressly incorporated herein by reference in their entirety: U.S. Provisional Application Ser. No. 62/533,362, (entitled STERILE PRODUCT BAG WITH FILTERED PORT); U.S. Provisional Application Ser. No. 62/533,380, (entitled DUAL CONTAINER SYSTEM FOR PRODUCT RECONSTITUTION); U.S. Provisional Application Ser. No. 62/533,427, (entitled FILTERED PRODUCT BAG WITH COMPACT FORM FACTOR); U.S. Provisional Application Ser. No. 62/533,440, (entitled MEDICAL SYRINGE SYSTEM WITH FILTERED FILLING PORT), each filed on Jul. 17, 2017.

FIELD OF THE DISCLOSURE

This disclosure relates to a sterile product bag and, in particular, a sterile product bag having an integral filter that allows microbial and particulate matter filtration during filling in non-traditional settings for the purposes of concentrate reconstitution.

BACKGROUND

Often, drugs and nutrients are mixed with a diluent before being delivered to a patient. The diluent may be, for example, a dextrose solution, a saline solution or even water. Many such drugs or nutrients are supplied in a concentrated form such as powder, liquid, gel, foam, etc., and packaged in glass or plastic vials.

In order for the concentrate to be administered to a patient, it must first undergo reconstitution. As used herein, the term reconstitution includes not only liquidization of non-liquid concentrates but also dilution of liquid concentrates.

In a predominant method of infusion therapy a drug or nutrient is present in liquid form as a solution contained in a parenteral solution container (e.g., an IV bag). The solution is intravenously administered to a patient using an administration set. The solution must be present in a sterile form upon administration to a patient. There are several methods for insuring the sterility of the solution. One primary method is to subject the container and solution to steam sterilization. However, numerous drugs and nutrients are not able to be subjected to the high temperatures applied during steam sterilization. The drug may deteriorate or form undesired by-products.

To avoid steam sterilization another method is to aseptically fill a sterile container with the solution. Rigorous sterility protocols must be followed to insure the solution being filled into the container has not been contaminated as the solution within each individual container is generally not tested to insure no contamination has occurred. Moreover some drugs will begin to deteriorate when placed in solution thus limiting the shelf life of the solution. To prevent or limit the deterioration, some solutions are frozen and then thawed into a liquid shortly before administration.

Whether sterilized by steam sterilization or aseptic filling, the volume and weight of the solution can lead to higher storage and transportation costs. Such costs can increase further if the solution must be stored and transported in a frozen state. Also some drugs deteriorate so rapidly in solution that the reconstitution of the drug into a solution must be done shortly before administration.

If the transportation and storage costs or the limited shelf life make providing a drug or nutrient in a pre-filled solution container, the drug or nutrient can be provided in a concentrated form in a vial for reconstitution shortly before administration. One way of reconstituting a concentrate is first to inject a diluent into the vial holding the concentrate. This may typically be performed by a syringe having a liquid diluent contained in the syringe barrel. After the rubber stopper of the vial is pierced by the syringe needle, the liquid is injected into the vial. The vial is shaken to reconstitute and dilute the concentrate with the liquid. The liquid is then withdrawn back into the syringe. These steps may be repeated several times to ensure complete reconstitution of the concentrate. After the final mixing, the syringe is withdrawn and the reconstituted product may then be injected into an IV bag container carrying a solution such as dextrose or saline. Such a reconstitution process must be conducted so that contamination is not introduced into the solution. The solution in the IV bag is then administered to the patient.

SUMMARY

One aspect of the present disclosure is directed to a medical product including a bladder, a filtration device, and a sterile product concentrate. The bladder has a perimeter seal and defining a sterile chamber. The filtration device includes a stem and a filter membrane disposed in line with the stem. The stem extends through the perimeter seal and has an inlet end accessible from outside of the perimeter seal and an outlet end in fluid communication with the sterile chamber. The filter membrane can have a nominal pore size in a range of approximately 0.1 µm to approximately 0.5 µm, wherein the filter membrane is shaped as a hollow fiber with a wall and pores residing in the wall of the fiber. The sterile product concentrate is disposed in the sterile chamber.

In some aspects, the product concentrate comprises a medicinal or nutritional concentrate.

In some aspects, the filter membrane is disposed inside of the stem between the inlet and outlet ends.

In some aspects, the filter comprises a plurality of filter membranes.

In some aspects, the outlet end of the hollow fiber of the filter membrane is sealed and the inlet end is an open inlet.

In some aspects, the filter membrane has a wall thickness in the range of approximately 150 µm to approximately 500 µm.

In some aspects, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In some aspects, the stem is one of a flexible stem or a rigid stem.

In some aspects, the stem is made of at least one of the following materials: PVC, PET, a poly(meth)acrylate, a polycarbonate, a polyolefin, a cycloolefin copolymer, polystyrene, or a silicone polymer.

In some aspects, the filtration device includes at least one U-shaped hollow fiber filter membrane secured in a U-shaped configuration by a filter membrane housing contained within a filter body.

In some aspects, the filtration device includes a plurality of U-shaped hollow fiber filter membranes.

In some aspects, the filtration device comprises a plurality of parallel hollow fiber membrane filters secured in a side-by-side configuration.

In some aspects, the filtration device comprises a plurality of parallel hollow fiber membrane filters arranged in a circular pattern.

In some aspects, the filter membrane has a nominal pore size in a range of approximately 0.1 µm to approximately 0.22 µm.

In some aspects, the chamber comprises at least a first chamber portion in fluid communication with the stem, and a second chamber portion isolated from the first chamber portion by an intermediate seal.

In some aspects, the product concentrate is disposed in the second chamber portion.

In some aspects, the bladder comprises adjacent front and rear films secured together by the perimeter seal, and the intermediate seal comprises a peelable seal formed by a bond between adjacent interior surface portions of the front and rear films, the peelable seal adapted to be broken to facilitate fluid communication between the first and second chamber portions.

In some aspects, the second chamber portion is not in fluid communication with the stem until the intermediate seal is broken.

In some aspects, the sterile chamber comprises a subdivided concentrate storage chamber in which the concentrate resides, the concentrate storage chamber in direct fluid communication with the stem.

Another aspect of the present disclosure includes a medical product including a bladder, a peelable seal, a filtration device, and a sterile product concentrate. The bladder has adjacent front and rear films secured together by a perimeter seal and defining a sterile chamber. The sterile chamber has at least a first chamber portion and a second chamber portion isolated from the first chamber portion by a peelable seal formed by a bond between adjacent interior surface portions of the front and rear films. The peelable seal is adapted to be broken to facilitate fluid communication between the first and second chamber portions. The filtration device includes a stem and a filter membrane disposed in line with the stem. The stem extends through the perimeter seal and having an inlet end accessible from outside of the perimeter seal and an outlet end in fluid communication with the sterile chamber. The filter membrane has a nominal pore size in a range of approximately 0.1 µm to approximately 0.5 µm, wherein the filter membrane is shaped as a hollow fiber with a wall and pores residing in the wall of the fiber. The sterile product concentrate is disposed in the second chamber portion of the sterile chamber.

In some aspects, the product concentrate comprises a medicinal or nutritional concentrate.

In some aspects, the filter membrane is disposed inside of the stem between the inlet and outlet ends.

In some aspects, the filtration device comprises a plurality of filter membranes.

In some aspects, the outlet end of the hollow fiber of the filter membrane is sealed and the inlet end is an open inlet.

In some aspects, the filter membrane has a wall thickness in the range of approximately 150 µm to approximately 500 µm.

In some aspects, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In some aspects, the stem is one of a flexible stem or a rigid stem.

In some aspects, the stem is made of at least one of the following materials: PVC, PET, a poly(meth)acrylate, a polycarbonate, a polyolefin, a cycloolefin copolymer, polystyrene, or a silicone polymer.

In some aspects, the filtration device includes at least one U-shaped hollow fiber filter membrane secured in a U-shaped configuration by a filter membrane housing contained within a filter body.

In some aspects, the filtration device includes a plurality of U-shaped hollow fiber filter membranes.

In some aspects, the filtration device comprises a plurality of parallel hollow fiber membrane filters secured in a side-by-side configuration.

In some aspects, the filtration device comprises a plurality of parallel hollow fiber membrane filters arranged in a circular pattern.

In some aspects, the filter membrane has a nominal pore size in a range of approximately 0.1 µm to approximately 0.22 µm.

Yet another aspect of the present disclosure includes a method of reconstituting a product from concentrate. The method includes providing a bladder having a perimeter seal and defining a sterile chamber containing a sterile product concentrate, a filtration device comprising a stem and a filter membrane, the stem extending through the perimeter seal and having an inlet end accessible from outside of the perimeter seal and an outlet end in fluid communication with the chamber, the filter membrane with a nominal pore size in a range of approximately 0.1 µm to approximately 0.5 µm, wherein the filter membrane is shaped as a hollow fiber with a wall and pores residing in the wall of the fiber. The method also includes introducing a pharmaceutical fluid into the chamber of the bladder through the filter membrane. The method also includes mixing the pharmaceutical fluid and the product concentrate together in the chamber of the bladder to reconstitute the product.

In some aspects, introducing the pharmaceutical fluid into the chamber of the bladder through the filter membrane comprises introducing the pharmaceutical fluid through a plurality of filter membranes.

In some aspects, introducing the pharmaceutical fluid into the chamber of the bladder through the filter membrane comprises introducing the pharmaceutical fluid through an open outlet end and a sealed outlet end of the hollow fiber of the filter membrane.

In some aspects, introducing the pharmaceutical fluid into the chamber of the bladder through the filter membrane comprises introducing the pharmaceutical fluid through a filter membrane having a wall thickness in the range of approximately 150 µm to approximately 500 µm.

In some aspects, introducing the pharmaceutical fluid into the chamber of the bladder through the filter membrane comprises introducing the pharmaceutical fluid through a filter membrane having a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, introducing the pharmaceutical fluid into the chamber of the bladder through the filter membrane comprises introducing the pharmaceutical fluid through a filter membrane made of at least one of the following materials: a polyolefin, polyvinylidene fluoride, polymethylmethacrylate, polyacrylonitrile, polysulfone, polyethersulfone, and a polymer containing cationic charges.

In some aspects, introducing the pharmaceutical fluid into the chamber of the bladder through the filter membrane comprises introducing the pharmaceutical fluid through a filtration device having at least one U-shaped hollow fiber filter membrane secured in a U-shaped configuration by a filter membrane housing contained within a filter body.

In some aspects, introducing the pharmaceutical fluid through a filtration device having at least one U-shaped hollow fiber filter membrane comprises introducing pharmaceutical fluid through a plurality of U-shaped hollow fiber filter membranes.

In some aspects, introducing the pharmaceutical fluid into the chamber of the bladder through the filter membrane comprises introducing the pharmaceutical fluid through a plurality of parallel hollow fiber membrane filters secured in a side-by-side configuration.

In some aspects, introducing the pharmaceutical fluid into the chamber of the bladder through the filter membrane comprises introducing the pharmaceutical fluid through a plurality of parallel hollow fiber membrane filters arranged in a circular pattern.

In some aspects, introducing the pharmaceutical fluid into the chamber of the bladder through the filter membrane comprises introducing the pharmaceutical fluid through a filter membrane having a nominal pore size in a range of approximately 0.1 µm to approximately 0.22 µm.

In some aspects, the method further includes providing the sterile chamber with at least a first chamber portion in fluid communication with the stem, and a second chamber portion containing the product concentrate and isolated from the first chamber portion by an intermediate seal, wherein introducing a pharmaceutical into the chamber of the bladder comprises introducing the diluent into the first chamber portion.

In some aspects, the method further includes sealing the bladder and removing the filter membrane from the bladder after introducing the pharmaceutical fluid through the filter membrane.

In some aspects, sealing the bladder and removing the filter membrane comprises sealing a portion of the stem of the filtration device to form a seal located between the bladder and the filter membrane and cutting the stem adjacent to the seal.

In some aspects, the method further includes performing a filter integrity test on the filter membrane after removing the filter membrane from of the product bag.

In some aspects, performing the filter integrity test comprises one of a pressure degradation test, a bubble point test, a water intrusion test, or a water flow test.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 1 is a front view of one embodiment of a medical product in accordance with the teachings of the present disclosure including a product bag containing a product concentrate and having a filtration device;

FIG. 2 is a right side view of the product bag of FIG. 1;

FIG. 3 is a front view of another embodiment of a medical product in accordance with the teachings of the present disclosure including a product bag containing a product concentrate and having a filtration device;

FIG. 4 is a right side view of the medical product of FIG. 3;

FIG. 13 is a front view of yet another alternative filtration device for the medical product of the present disclosure including a plurality of hollow fiber membranes secured side by side;

FIG. 14 is an isometric view of the securement device used for the plurality of hollow fiber membranes depicted in FIG. 13;

FIG. 16 is an exploded perspective view of an alternative connector for use with a three-filter filter bundle;

FIG. 17 is a side exploded view of the connector of FIG. 16;

FIG. 21 illustrates a first alternative sealing arrangement for a filtered stem of the sterile product bags of FIGS. 1-4, showing the filtered stem prior to engagement with a filling nozzle;

FIG. 22 illustrates the sealing arrangement of FIG. 21, showing the filtered stem during engagement with a filling nozzle;

FIG. 23 illustrates a second alternative sealing arrangement for a filtered stem of the sterile product bags of FIGS. 1-4, showing the filtered stem in a closed and sealed configuration prior to filling a downstream product chamber;

FIG. 24 illustrates the sealing arrangement of FIG. 23, showing the filtered stem cut in an open and unsealed configuration;

FIG. 25 illustrates the sealing arrangement of FIGS. 23 and 24, showing the filtered stem cut in an open and unsealed configuration and engaged with a filling nozzle for filling the downstream product chamber;

FIG. 26 illustrates the sealing arrangement of FIGS. 23-25, showing the filtered stem subsequent to filling where tubing located downstream of the filter has been sealed closed;

FIG. 27 illustrates the sealing arrangement of FIGS. 23-26, showing the downstream tubing cut away from the downstream product chamber to facilitate integrity testing of the filter;

DETAILED DESCRIPTION

Figure 5:
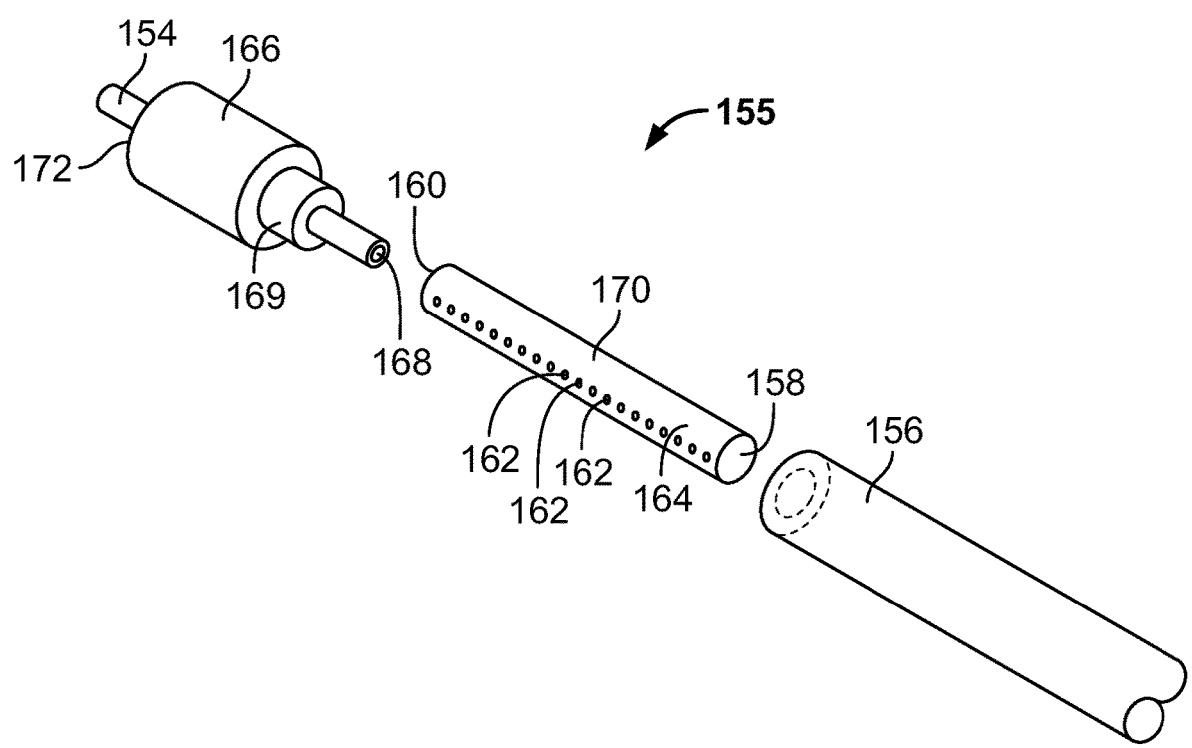
FIG. 5 is an expanded isometric view of the filtration device depicted in FIGS. 3 and 4.
Figure 6:
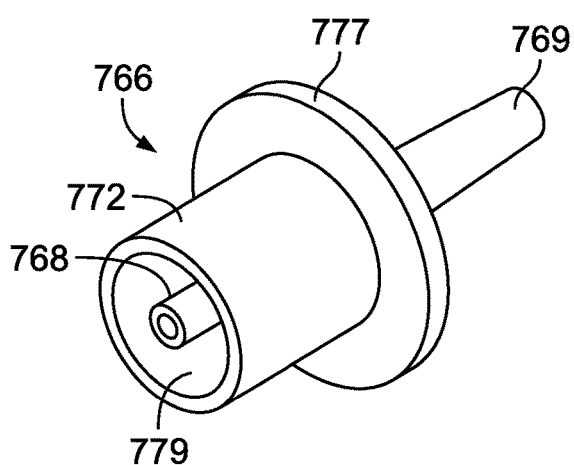
FIG. 6 is a perspective view of an alternative connector for use with a filtration device such as that disclosed in FIGS. 3-5.
Figure 7:
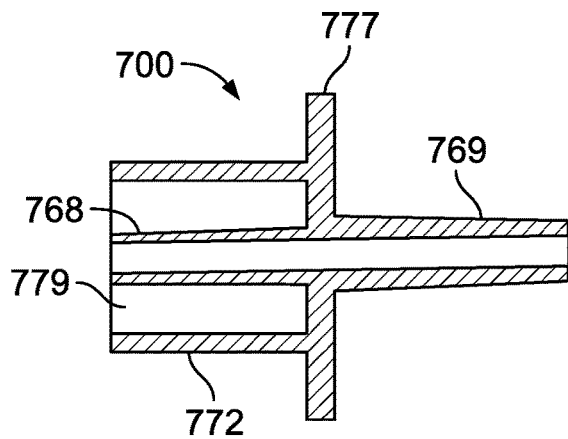
FIG. 7 is a side cross-sectional view of the connector of FIG. 6.
Figure 8:
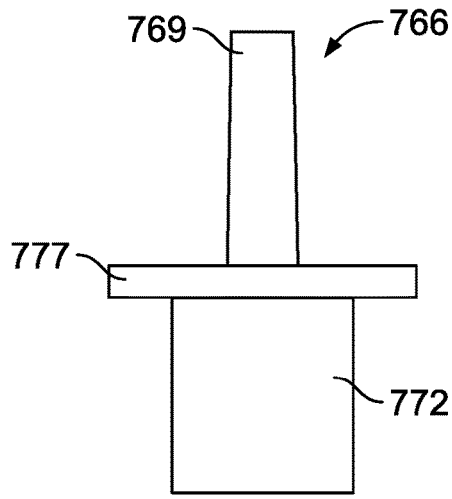
FIG. 8 is a side view of the connector of FIG. 6.
Figure 9:
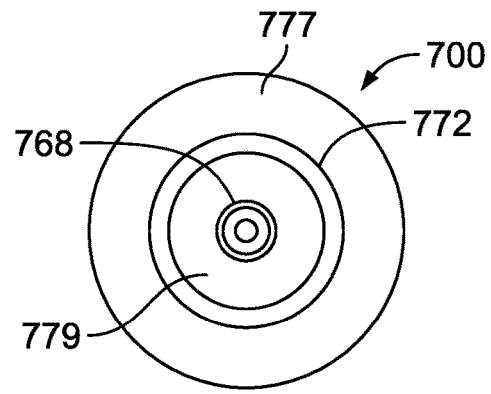
FIG. 9 is a bottom view of the connector of FIG. 8.
Figure 10:
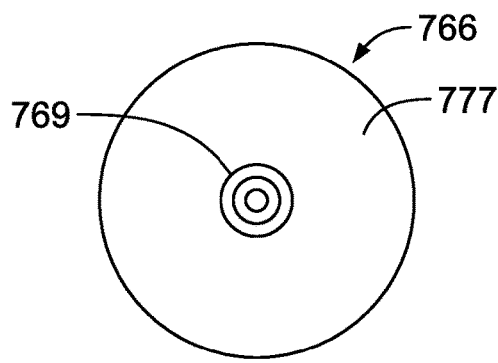
FIG. 10 is a top view of the connector of FIG. 8.

The present disclosure is directed to a novel medical product and method of using the product to reconstitute a concentrate in the product bag. Generally, the medical product includes a product bag that includes at least one chamber that is provided to a hospital or pharmacist, for example, with a product concentrate pre-filled and sealed in the chamber. On demand, the pharmacist can introduce a medical fluid such as a diluent into the pre-filled chamber through a sterilization filter such that the fluid is sterilized and resident in the chamber with the product concentrate. Subsequently, the product concentrate and diluent can be mixed thoroughly to reconstitute the product prior to patient administration. One benefit of this arrangement is that the product bag can be provided to the pharmacist pre-filled with a sterile product concentrate, and the diluent or other pharmaceutical can be added on-demand. Avoiding the shipment and storage of the liquid diluent can substantially decrease shipping and storage costs. Moreover, because the diluent is provided to the bag on-demand, the sterility and integrity of the diluent over the course of shipping and storing the product bag is no longer a concern. Finally, this allows for pre-filling, shipment and storage of product in a concentrated form such as a powder or granular form which can illustrated increased stability and shelf life over liquid forms.

To meet the foregoing, the present disclosure provides three different embodiments of sterile product bags. A first embodiment described primarily with reference to FIGS. 1-4 includes a single-chamber product bag pre-filled with a concentrate. With a single-chamber product bag delivered to the hospital or pharmacist requires the introduction of diluent to the bag, as suggested above. A second embodiment of the disclosure described primarily with reference to FIGS. 34 and 35 includes a product bag with two chamber portions separated by a "peelable seal." With this configuration, the first chamber portion is provided to the hospital or pharmacist completely empty and communicates with a filtered inlet port for introducing diluent to the first camber portion on-demand. The second chamber portion can be pre-filled with the sterile concentrate. Once the diluent has been introduced into the first chamber portion, hydraulic pressures can be created by squeezing the bag to break the "peelable seal" and intermix the contents of the two chamber portions to reconstitute the concentrate prior to administration to the patient. A third embodiment of the disclosure described primarily with reference to FIGS. 36-44 includes a product bag similar to the two chamber bag in FIGS. 34 and 35, but it is also described as including a third chamber portion disposed adjacent to an outlet or administration port, and the chamber portions where the fluids are mixed prior to delivery. This third chamber portion can serve as a security interface for the outlet or administration port. Each of these embodiments will now be described in more detail.

FIGS. 1 and 2 illustrate a first embodiment of a medical product 101 including a sterile product bag 100 pre-filled a product concentrate 105. The product bag 100 includes a pre-sterilized interior defined by a bladder 102, and also includes a filtration device 106. The filtration device 106 of the present embodiment includes a stem 156, a filter membrane 142 disposed in-line with the stem 156, and a sterile closure cap 108. The bladder 102 is a fillable pouch having an interior chamber 103 having a standard volume capacity with the pre-sterilized inner environment. At least partially surrounding a perimeter of the fillable pouch is a sealed perimeter 110 having a plurality of apertures 112 configured to receive mounting hang pins during filling, administration, and/or storage. The chamber 103 of the bladder 102 is fluidly connected to the stem 156 at an opening 114 at a first end 116 of the bladder 102. An administration port 118 and an addition port 120 for adding pharmaceutical substances into the bladder are disposed at a second end 122 of the bladder 102. By way of example only, the addition port 120 may include a vial adaptor, a med port with a solid septum or a Luer-Activated-Device (LAD), which can also be referred to as a Luer-Activated-Valve (LAV). Other ports can be included as desired.

The stem 156 of the filtration device 106 is a hollow narrow tube having an inlet 124 fluidly connected to the opening 114 of the bladder 102. The stem 156 can include a tapered head 126 defining the inlet 124, a collar 128 connecting a first stem part 130 to the tapered head 126, a second part 132, and a duct 134 defining a stem outlet 136. The sterile closure cap 108 has a hemispherical shaped knob 138 attached to a neck 140 that sealably covers the inlet 124 of the stem 156 to maintain sterility until necessary to remove the knob 138 for filling. The tapered head 126 may be a female fitting adapted for sealingly engaging a Luer fitting of a fluid supply line during filling, for example. The filter membrane 142 of the version depicted in FIGS. 1 and 2 includes a flat sheet membrane disposed in-line with the stem 156 between the first and second parts 130, 132 of the stem 156. Non-limiting examples of acceptable filter membranes for the filter membrane 142 are disclosed in U.S. Patent Publication No. 2012/0074064 A1 and PCT Publication No. PCT/EP2015/068004, the entire contents of which are incorporated herein by reference.

So configured, a pharmaceutical fluid such as a water, saline, a solution, a diluent, a final drug product, etc., may enter the filtration device 106 via the inlet 124 of the stem 156 and pass through the head 126 and into the first part 130 toward an inlet 144 of the filter membrane 142. The fluid then filters through the filter membrane 142, out an outlet 146, and into the second part 132 of the stem 156. The duct 134 carries the filtered solution from the second part 132 to the opening 114 of the bladder 102, which leads to the sterile chamber 103, which is pre-filled with the product concentrate 105.

The second part 132 of the stem 156 defined as the area of the stem between the outlet of the filter membrane 142 and an inlet 148 of the duct 134 may be identified as a "seal and cut area." The phrase "seal and cut area" pertains to the manner in which the product bag 100 is sealed and cut after introducing fluid to the chamber 103 through the filtration device 106. That is, the disclosed arrangement is designed such that after the bladder 102 receives fluid from the filtration device 106, a sealing mechanism can be employed to seal the stem 156 closed in the "seal and cut area," which is below the filter membrane 142 but above the bladder 102. Thus, the "seal and cut area" 132 in this version is a portion of the stem 156 above the bladder 102 where the filtration device 106 does not reside. Sealing of the "seal and cut area" 132 can be achieved with a heat sealer or any other device, including for example clamping a clamp onto the "seal and cut area" 132. Once the stem 156 is sealed, the stem 156 is cut at a location above the seal but below the filter membrane 142. Cutting may be achieved with a knife or any other device. The stem 156 provides an isolated fluid connection between the inlet 124 and the chamber 103 of the bladder 102, such that once the fluid is filtered through the filter membrane 142, the filtered fluid passes directly into the sterilized environment of the pre-filled chamber 103 of the bladder 102. Hence, after the bladder 102 receives the sterilized fluid and the stem 156 is sealed and cut, the fluid and product concentrate 105 in the bladder 102 remains sterile until the bladder 102 is punctured or compromised. This, of course, assumes that the filtration device 106 was uncompromised prior to filling and performed as desired.

To ensure that the filtration device 106 performed properly, a filter integrity test can be performed on the filter membrane 142. A filter integrity test is facilitated by the arrangement of the "seal and cut area" (second part 132) of the stem 156, which allows for the filter membrane 142 to be separated intact from the remainder of the now-sealed bladder 102. For example, after the stem 156 and filtration device 106 are separated from the product bag 100, a filter testing device (not shown) may be pre-programmed or controlled to perform a filter integrity test on the filter membrane 142. Examples of filter integrity tests might include a bubble point test, a pressure degradation test, a water intrusion test, a water flow test, or any suitable test known in the art. A pressure degradation test is a method for testing the quality of a filter either before or after the filter has been used. In the preferred embodiment, the filtration device 106 is tested after the solution passes through the filter membrane 142 and into the bladder 102 of the product bag 100. To perform the filter integrity test using a pressure degradation test procedure, a test head (not shown) engages the stem 156 and applies an air pressure of a predetermined value to the inlet 124 and filter membrane 142. In one embodiment, the pre-determined value is the pressure where gas cannot permeate the filter membrane 142 of an acceptable filtration device 106. A pressure sensor, or other method of measuring the integrity of the filter, is located within the test head and measures the pressure decay or diffusion rate through the filter membrane 142. The results from the integrity test are assessed to determine the quality of the filtration device 106, and therefore the quality of the solution that previously passed through the filtration device 106 and into the product bag 100. If the pressure sensor measures a decay or a unexpected rate of decay, then the filtration device 106 fails the test and it can be determined that the solution in the product bag is unsatisfactory. Alternatively in a bubble point test, the test head gradually increases the pressure applied to the filtration device 106, and the increase in pressure is measured in parallel with the diffusion rate of the gas through the filter membrane 142. Any disproportionate increase in diffusion rate in relation to the applied pressure may indicate a hole or other structural flaw in the filter membrane 142, and the filter would fail the integrity test.

Thus, it can be appreciated that the disclosed arrangement of the "seal and cut area" 132 disclosed herein advantageously facilitates the filter integrity test, and a determination that the fluid in the product bag is either sterile or has the potential of being compromised may be made with a high degree of certainty.

An alternative medical product 101 of the present disclosure is illustrated in FIGS. 3-5, which includes a sterile product bag 150 containing a product concentrate 105. The product bag 150 has a similar bladder 152 defining a chamber 153 and sterile closure cap 154 as that of the first product bag 100. In FIGS. 3-5, the product bag 150 includes a filtration device 155 including a filter membrane 170 is disposed within (i.e., at least partially or entirely inside of) a stem 156. The stem 156, which may be tapered or cylindrical, does not provide a separate inlet and outlet connection ports for the filtration device 155 as illustrated in the product bag 100 of FIGS. 1 and 2. Instead, as shown in FIG. 5, the filter membrane 170 of the filtration device 155 can be a hollow fiber membrane with one sealed end 158 and one open inlet end 160. The sealed end 158 can be capped or it may be sealed with a heat seal, an adhesive, or some other means. A plurality of pores 162 along the surface 164 of the filtration device 155 allow a pharmaceutical fluid that entered the filtration device 155 at the open inlet end 160 to exit the filtration device 155. In one version, the stem 156 surrounds the filter membrane 170 in a generally concentric configuration so filtered pharmaceutical fluid exiting the filter membrane 170 is contained within the stem 156 and ultimately passed into the bladder 152. Again, like in FIGS. 1 and 2, the product bag in FIGS. 3-5 includes a "seal and cut area" 132 below the filtration device 155 and above a bladder 152, wherein the "seal and cut area 132" facilitates separation of that portion of the stem 156 containing the filter membrane 170. Because the "seal and cut area" 132 exists, the filter membrane 170 can be separated intact. As described above with respect to FIGS. 1 and 2, this "seal and cut area" 132 can advantageously facilitate an integrity test procedure on the filtration device 155.

As depicted in FIG. 5, a hollow connector 166 can be used to secure the stem 156 and the components of the filtration device 155 together. The open inlet end 160 of the filter membrane 170 is sealingly connected to an open outlet end 168 of the hollow connector 166. The connection may be achieved by gluing the open inlet end 160 of the filter membrane 170 to the open outlet end 168 of the connector 166 with, for example, an epoxy resin, a polyurethane resin, a cyanoacrylate resin, a UV curing acrylic adhesive, or a solvent for the material of the hollow connector 166 such as cyclohexanone. In the version depicted, the open outlet end 168 of the connector 166 comprises a hollow cylindrical member that fits inside of and is fixed to the open inlet end 160 of the filter membrane 170. As such, an outer diameter of the open outlet end 168 of the connector 166 is substantially similar to or slightly smaller than an inner diameter of the open inlet end 160 of the filter membrane 170. In some versions, the open inlet end 160 of the filter membrane 170 may be welded to the open outlet end 168 of the connector 166 by, for example, heat welding (e.g., introducing a hot conical metal tip into the open inlet end 150 of the filter membrane 170 to partially melt it), laser welding if the hollow connector 166 is made from a material that absorbs laser radiation, mirror welding, ultrasound welding, and friction welding. Alternately, the filter membrane 170 may be inserted into a mold, and a thermoplastic polymer may be injection-molded around it to form the hollow connector 166. Other designs and configurations for connecting the components of the filtration device 155 together are intended to be within the scope of the present disclosure.

The hollow connector 166 further includes a fluid inlet 169. A pharmaceutical fluid can be fed via a connected fluid supply line, for example, into the fluid inlet 169 of the hollow connector 166. In some versions, the fluid inlet 169 can include a Luer type fitting or other standard medical fitting. The pharmaceutical fluid can then travel through the hollow connector 166 and exit into the filter membrane 170 through the open outlet end 168 of the hollow connector 166. The hollow connector 166 also includes a sealing surface 172 to which the stem 156 is attached. The sealing surface 172 in this version is cylindrical and has a diameter larger than a diameter of the open outlet end 168, and is disposed generally concentric with the open outlet end 168. In fact, in this version, the outer diameter of the sealing surface 172 is generally identical to or slightly smaller than an inner diameter of the stem 156. So configured, the stem 156 receives the sealing surface 172 and extends therefrom to surround and protect the filter membrane 170 without contacting the surface 164 of the filter membrane 170. The stem 156 can be fixed to the sealing surface 172 with adhesive (e.g., a UV curing acrylic adhesive), epoxy, welding, bonding, etc. The stem 156 receives the pharmaceutical solution after it passes through the pores 162 in the filter membrane 170. From there, the now filtered solution passes into the bladder 152.

FIGS. 6-10 illustrate an alternative hollow connector 766, similar to connector 166, for securing the stem 156 and the hollow fiber filter membrane 170 of FIGS. 3-5 together. The connector 766 includes an open outlet end 768 carried by a stem structure that extends in a first direction from a bearing plate 777 and is adapted to be sealingly connected to the open inlet end 160 of the filter membrane 170. The connection may be achieved by gluing the open inlet end 160 of the filter membrane 170 to the open outlet end 768 of the connector 766 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet end 768 of the connector 766 comprises a hollow cylindrical member that fits inside of and is fixed to the open inlet end 160 of the filter membrane 170. As such, an outer diameter of the open outlet end 768 of the connector 766 is substantially similar to or slightly smaller than an inner diameter of the open inlet end 160 of the filter membrane 170. In some versions, the open inlet end 160 of the filter membrane 170 may be welded to the open outlet end 768 of the connector 766 by, for example, heat welding (e.g., introducing a hot conical metal tip into the open inlet end 150 of the filter membrane 170 to partially melt it), laser welding if the hollow connector 766 is made from a material that absorbs laser radiation, mirror welding, ultrasound welding, and friction welding. Alternately, the filter membrane 170 may be inserted into a mold, and a thermoplastic polymer may be injection-molded around it to form the hollow connector 766. Other designs and configurations for connecting the filter membrane 170 to the connector 766 are intended to be within the scope of the present disclosure.

The hollow connector 766 further includes a fluid inlet 769, which is also a stem structure, extending in a second direction (opposite the first direction) from the bearing plate 777. A pharmaceutical fluid can be fed via a connected fluid supply line, for example, into the fluid inlet 769 of the hollow connector 766. In some versions, the fluid inlet 769 can include a Luer type fitting or other standard medical fitting. The pharmaceutical fluid can then travel through the hollow connector 766 and exit into the filter membrane 170 through the open outlet end 768 of the hollow connector 766.

The hollow connector 766 also includes a sealing surface 772 to which the stem 156 is attached. The sealing surface 772 in this version is a cylindrical shroud extending from the bearing plate 777 in the first direction and has a diameter larger than a diameter of the open outlet end 768. The sealing surface 772 is disposed generally concentric with the open outlet end 768. As such, in this embodiment, the shroud of the sealing surface 772 surrounds the stem structure of the open outlet end 768 such that an annular gap 779 resides between the two. In fact, in this version, the outer diameter of the sealing surface 772 is generally identical to or slightly smaller than an inner diameter of the stem 156. So configured, the sealing surface 772 of the connector 766 can be received by the stem 156 such that the stem 156 extends therefrom to surround and protect the filter membrane 170 without contacting the surface 164 of the filter membrane 170. The stem 156 can be fixed to the sealing surface 772 with adhesive (e.g., a UV curing acrylic adhesive), epoxy, welding, bonding, etc. The stem 156 receives the pharmaceutical fluid after it passes through the pores 162 in the filter membrane 170. From there, the now filtered fluid passes into the bladder 152 in the same manner described above with respect to FIGS. 3-5.

While the foregoing version of the filtration device 155 has been described as including a single filter membrane 170, in other embodiments within the scope of the present disclosure, the filtration device 155 may include multiple filter membranes 170. A few non-limiting examples of multiple membrane filters will be discussed below. Finally, as described with respect to the product bags 100, 150 in FIGS. 1-4, the connector 166 in FIG. 5 can include a sterile closure cap 154 covering the solution inlet 160 to prevent contaminants from entering the product bag prior to being filled.

In one version of the foregoing assembly of FIG. 5, and as mentioned, the stem 156 includes an inner diameter that is larger than an outer diameter of the filter membrane 170, and the stem 156 includes a longitudinal dimension that is larger than a longitudinal dimension of the filter membrane 170. As such, when the stem 156 and filter membrane 170 are assembled onto the connector 166, the filter membrane 170 resides entirely within (i.e., entirely inside of) the stem 156 and a gap exists between the inner sidewall of the stem 156 and the outer sidewall of the filter membrane 170. As such, fluid passing into the filter membrane 170 passes out of the plurality of pores 162 and flows without obstruction through the gap and along the inside of the stem 156 to the bladder. In some versions, the stem 156 can be a flexible tube, a rigid tube, or can include a tube with portions that are flexible and other portions that are rigid. Specifically, in some versions, a stem 156 with at least a rigid portion adjacent to the filter membrane 170 can serve to further protect the filter membrane 170 and/or prevent the filter membrane 170 from becoming pinched or kinked in a flexible tube. In other versions, such protection may not be needed or desirable. In one embodiment, the stem 156 has an internal diameter in the range of approximately 2.5 mm to approximately 8 mm, and a longitudinal dimension in the range of approximately 5 cm to approximately 30 cm. In one embodiment, the internal diameter of the stem 156 is about 0.2 to about 3 mm larger than the outer diameter of the filter membrane 170. And, the filter membrane 170 has an outer diameter in the range of approximately 2.3 mm to approximately 5 mm, a longitudinal dimension in the range of approximately 3 cm to approximately 420 cm, and a wall thickness in the range of approximately 150 µm to approximately 500 µm. Furthermore, in one version each of the plurality of pores 162 in the filter membrane 170 have a diameter less than or equal to approximately 0.2 microns. In some versions, each pore has a diameter less than or equal to a value in a range of approximately 0.1 microns to approximately 0.5 microns, for instance, approximately 0.2 to approximately 0.4 microns. In some versions, each pore has a diameter that is less than or equal to approximately microns. In some versions, each pore has a diameter that is less than or equal to a value in a range of approximately 0.1 microns to approximately 0.2 microns. In some versions, each pore has a diameter that is less than or equal to a value in a range of approximately 0.1 microns to approximately 0.22 microns. These pore sizes coupled with the disclosed geometrical dimension of the stem 156 and filter membrane 170 ensure acceptable flow rates through the filter membrane 170 for filling the product bags with patient injectable solutions such as sterile water, sterile saline, etc. In other versions, any or all of the dimensions could vary depending on the specific application.

Suitable materials for the filter membrane 170 can include polyolefins (e.g., PE, PP), polyvinylidene fluoride, polymethylmethacrylate, polyacrylonitrile, polysulfone, and polyethersulfone. In some embodiments within the scope of the present disclosure, the filtration device 155 may be comprised of a blend of polysulfone or polyethersulfone and polyvinylpyrrolidone. In other embodiments within the scope of the present disclosure, the filter membrane 170 can include a polymer containing cationic charges, e.g. polymers bearing functional groups like quaternary ammonium groups. A suitable example for such polymers is polyethyleneimine. The filter membrane 170 may be manufactured by known techniques including, e.g., extrusion, phase inversion, spinning, chemical vapor deposition, 3D printing, etc. Suitable materials for the stem 156 include PVC, polyesters like PET, poly(meth)acrylates like PMMA, polycarbonates (PC), polyolefins like PE, PP, or cycloolefin copolymers (COC), polystyrene (PS), silicone polymers, etc.

Additional details regarding some possible versions of the filter and the specific construction of the membrane, for example, can be found in European Patent Application No. EP16152332.9, entitled FILTER MEMBRANE AND DEVICE, filed Jan. 22, 2016, and additionally in PCT/EP2017/051044, entitled FILTER MEMBRANE AND DEVICE, filed Jan. 19, 2017, the entire contents of each of which are expressly incorporated herein by reference.

Thus far, the hollow fiber membrane 170 in FIG. 5, for example, has been described as being located within the stem 156. In other embodiments, the filtration device 155 may include its own housing or other support structure, which is coupled to the stem 156 either in place of the connector 166 in FIG. 5 or connector 766 in FIGS. 6-10, or at a location between two portions of the stem 156.

Figure 11:
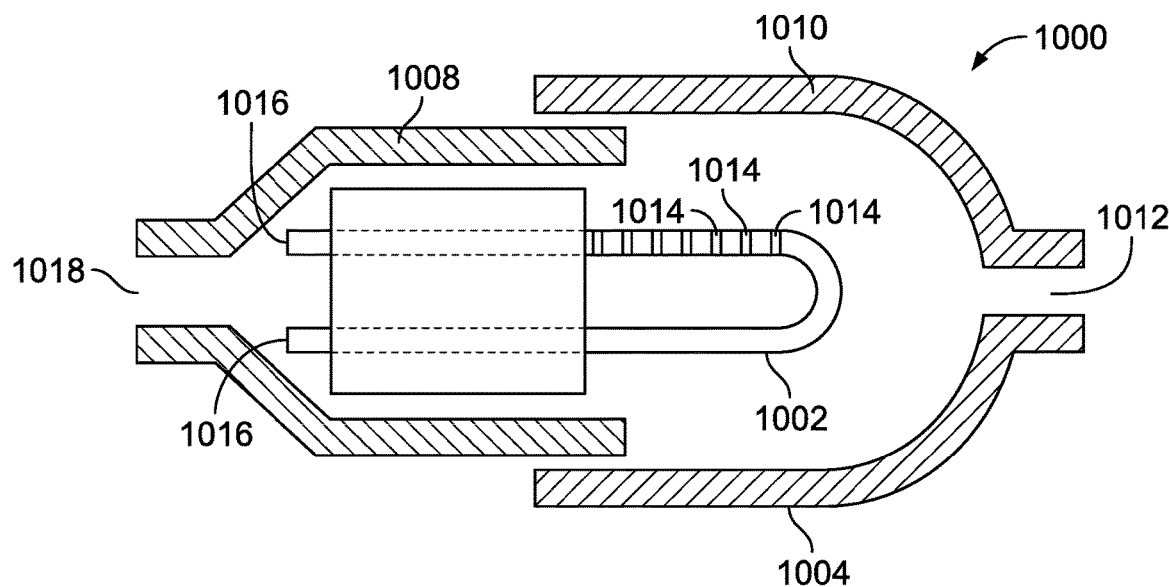
FIG. 11 is a front view of an alternative filtration device for the medical product of the present disclosure having a single looped hollow fiber membrane contained within a filter body.

For example, FIG. 11 is a front view of a filter assembly 1000 for use in a filtration device between portions of a stem, and having a single U-shaped hollow fiber filter membrane 1002 contained within a filter body 1004. The filter membrane 1002 is secured to a filter membrane housing 1006 in the U-shaped configuration with an adhesive (i.e., a UV curing acrylic adhesive), an epoxy, welding, bonding, or other means. The filter membrane housing 1006 is connected to the filter body 1004 at an outlet portion 1008 of the filter body 1004. An inlet portion 1010 is sealably connected to the outlet portion 1008 of the filter body 1004 at a joint or other seam. The inlet portion 1010 of the filter body 1004 has an inlet 1012 by which a pharmaceutical fluid may enter the filter assembly 1000. The pharmaceutical fluid then enters the filter membrane 1002 through a plurality of pores 1014, travels through the filter membrane 1002, exits the filter membrane 1002 at filter membrane outlets 1016, and exits the filter body 1004 at filter outlet 1018. The filter outlet 418 may then be connected to the bladder (not pictured) via the stem 256 of a product bag (not pictured). In FIG. 11, the flow of fluid through the assembly 1000 has been described as moving from the inlet 1012 of the inlet portion 1010 to the outlet 1018 of the outlet portion 1008. However, the same assembly 400 could be used in the opposite direction such that fluid enters the outlet 1018 of the outlet portion 1008 and exits the inlet 1012 of the inlet portion 1010. In this alternative configuration, fluid would first enter the inlet 1012, pass into the filter membrane 1002 at the filter membrane outlets 1016, and exit through the pores 1014 and finally the inlet 1012.

Figure 12:
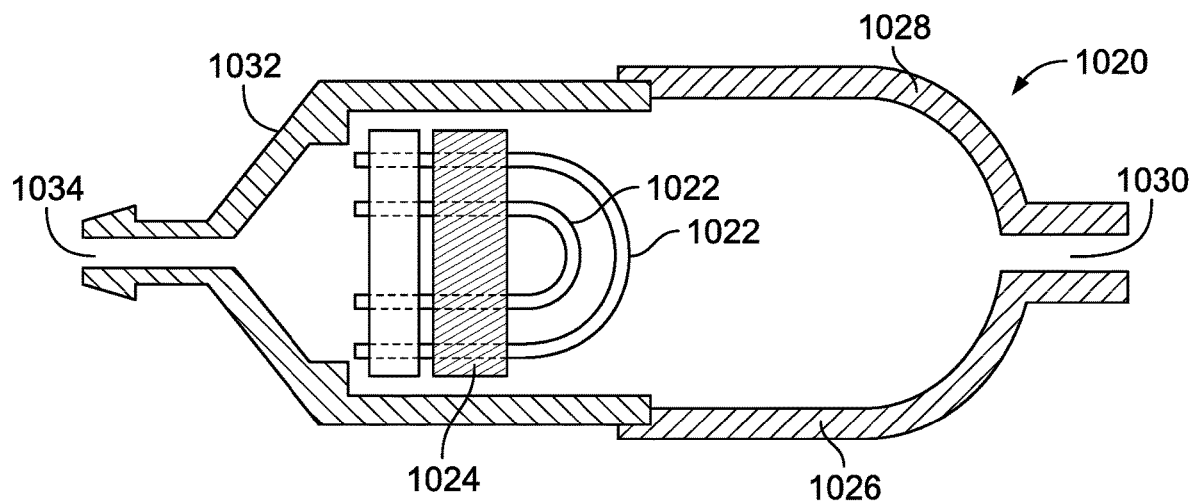
FIG. 12 is a front view of is a front view of another alternative filtration device for the medical product of the present disclosure having a plurality of looped hollow fiber membranes contained within a filter body.

FIG. 12 is an alternate embodiment of the filter assembly 1000 depicted in FIG. 11. In FIG. 12, the filter 1020 includes two U-shaped hollow fiber filter membranes 1022 are secured to a filter membrane housing 1024 in the U-shaped configuration with an adhesive (i.e., a UV curing acrylic adhesive), an epoxy, welding, bonding, or some other means. The filter membranes 1022 and filter membrane housing 1024 are contained within a filter body 1026 having an inlet portion 1028 with inlet 1030 sealably connected to an outlet portion 1032 having filter outlet 1034. In other embodiments, a filter may include more than two U-shaped hollow fiber filter membranes arranged as depicted in FIGS. 11 and 12. In FIG. 12, like in FIG. 11, the flow of fluid through the assembly 1000 has been described as moving from the inlet portion 1028 to the outlet portion 1032. However, the same assembly 1000 could be used in the opposite direction such that fluid enters the outlet portion 1032 and exits the inlet portion 1028 as described above relative to FIG. 11.

FIG. 13 is a further alternative filter assembly. Specifically, in FIG. 13, a plurality of linear filter membranes 502 are secured directly together in a parallel side-by-side configuration for what can be referred to as a fiber bundle. The filter membranes 502 in FIG. 13 can be secured together with adhesive (i.e., a UV curing acrylic adhesive), epoxy, welding, bonding, etc. In other versions, the plurality of filter membranes 502 can be manufactured together as one piece by way of any of the manufacturing techniques described above.

FIG. 14 provides another alternative in which a securement device 504 includes a number of blocks defining a plurality of grooves 506 identical to the number of hollow fiber filter membranes 502. The blocks of the securement device 504 may be sandwiched together and used to hold the plurality of hollow fiber filter membranes 502 in the sideby-side configuration. The securement device 504 depicted in FIG. 14 allows for two sets of the hollow fiber filter membranes 502 of FIG. 13 to be stacked relative to each other. The fiber bundle including the filter membranes 502 and the securement device 504 may be placed in a filter body, such as that discussed with respect to FIGS. 11 and 12.

Figure 15:
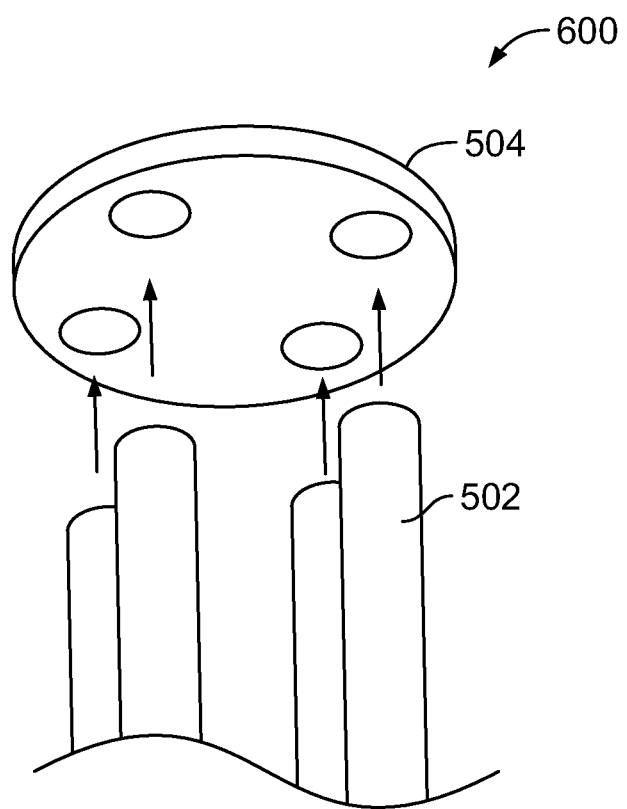
FIG. 15 is an isometric view of still another alternative filtration device for the medical product of the present disclosure including fiber bundle for a product bag having a plurality of hollow fiber membranes secured in a circular holder.

FIG. 15 is an isometric view of another version of a fiber bundle 600 for a product bag (not pictured) having a plurality of parallel hollow fiber filter membranes 502 similar to FIGS. 13 and 14, but wherein the parallel filter membranes 502 are arranged in a circular pattern by a circular holder 504. The fiber bundle 600 may be placed in a filter body, such as that discussed with respect to FIGS. 11 and 12.

FIGS. 16-17 and FIGS. 18-20 illustrate two additional devices for coupling fiber bundles to a stem in accordance with the present disclosure. FIGS. 16-17 discloses a connector 866 for connecting a three-fiber bundle to a stem. Specifically, the connector 866 includes a first hollow body 866a and a second hollow body 866b. The first body 866a includes a solution inlet 869, which is a stem structure, extending from a bearing plate 877. A pharmaceutical fluid can be fed via a connected fluid supply line, for example, into the fluid inlet 869 of the first hollow body 866a of the connector 866. In some versions, the fluid inlet 869 can include a Luer type fitting or other standard medical fitting.

The hollow connector 866 also includes a sealing surface 872 to which the stem 156 is attached. The sealing surface 872 in this version is a cylindrical shroud extending from the bearing plate 877 in a direction opposite to a direction of extension of the fluid inlet 869. The sealing surface 872 is disposed generally concentric with the fluid inlet 869. As such, in this embodiment, the shroud of the sealing surface 872 defines a cylindrical cavity (not shown in the drawings) for receiving a portion of the second hollow body 866b of the connector 866.

The second hollow body 866b, as depicted, includes a support plate 880 and three open outlet ends 868 extending from the support plate 880. Additionally, the support plate 880 includes an outer diameter that is essentially the same as or slightly smaller than an inner diameter of the cavity of the shroud of the sealing surface 872 such that when assembled, the support plate 880 is positioned into the cavity. In one version, the support plate 880 includes a seal member 882 around its periphery to form a fluid tight seal with the inner surface of the shroud of the sealing surface 872 when inserted into the cavity. Friction, adhesive, or some other means may retain the support plate 880 in connection with the shroud of the sealing surface 872.

As mentioned, the second body 866b includes three open outlet ends 868 extending from the support plate 880. Each open outlet end 868 is adapted to be sealingly connected to an open inlet end 160 of one of three filter membranes 170. The connection may be achieved by gluing open inlet ends 160 of the filter membranes 170 to the open outlet ends 868 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet ends 868 of the connector 866 comprises a hollow cylindrical member that fits inside of and is fixed to the open inlet ends 160 of the filter membranes 170. As such, an outer diameter of the open outlet ends 868 is substantially similar to or slightly smaller than an inner diameter of the open inlet ends 160 of the filter membrane. In some versions, the filter membranes 170 may be welded to the open outlet ends 868 of the connector 866 by, for example, heat welding (e.g., introducing a hot conical metal tip into the open inlet ends 150 of the filter membranes 170 to partially melt it), laser welding if the hollow connector 866 is made from a material that absorbs laser radiation, mirror welding, ultrasound welding, and friction welding. Alternately, the filter membranes 170 may be inserted into a mold, and a thermoplastic polymer may be injection-molded around it to form the hollow connector 866. Other designs and configurations for connecting the filter membranes 170 to the open outlet ends 868 are intended to be within the scope of the present disclosure.

Finally, as with previously described embodiments, the sealing surface 872 of the connector 866 can be received by the stem 156 such that the stem 156 extends therefrom to surround and protect the filter membranes 170 without contacting the surfaces 164 of the filters 155. The stem 156 can be fixed to the sealing surface 872 with adhesive (e.g., a UV curing acrylic adhesive), epoxy, welding, bonding, etc. The stem 156 receives the pharmaceutical solution after it passes through the pores 162 in the filter membranes 170. From there, the now filtered solution passes into the bladder 152 in the same manner described above with respect to FIGS. 3-5.

Figure 18:
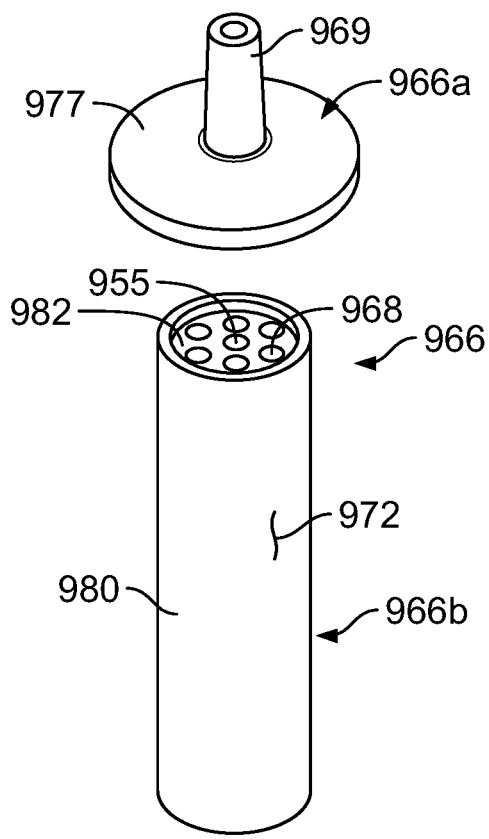
FIG. 18 is a exploded perspective view of another alternative connector for use with a seven-filter filter bundle.
Figure 19:
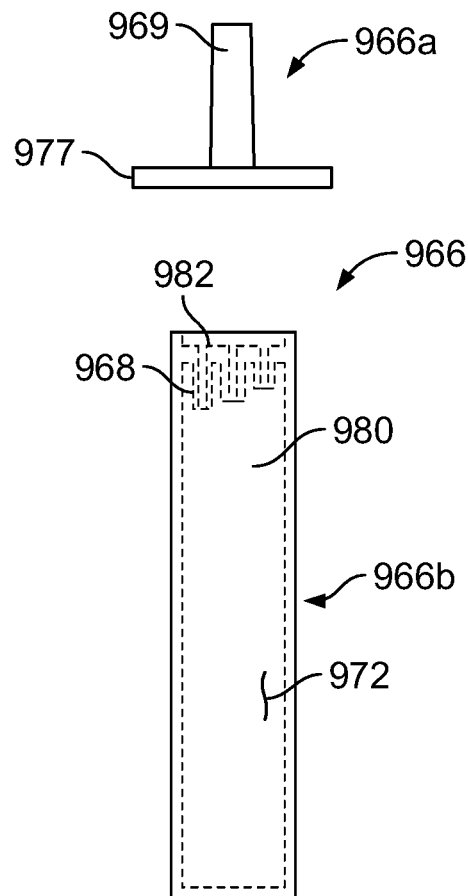
FIG. 19 is a side exploded view of the connector of FIG. 18.
Figure 20:
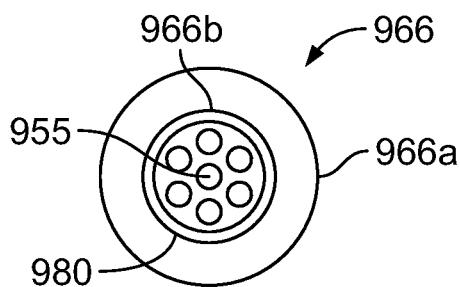
FIG. 20 is a bottom view of the connector of FIG. 19.

FIGS. 18-20 discloses a connector 966 for connecting a seven-fiber bundle to a stem. Specifically, the connector 966 includes a first hollow body 966a and a second hollow body 966b that can be connected to the first hollow body 966a with an adhesive or via other means. The first body 966a includes a solution inlet 969, which is a stem structure, extending from a bearing plate 977. A pharmaceutical fluid can be fed via a connected fluid supply line, for example, into the fluid inlet 969 of the first hollow body 966a of the connector 966. In some versions, the fluid inlet 969 can include a Luer type fitting or other standard medical fitting.

The second hollow body 966b, as depicted, includes a hollow cylindrical support collar 980 in which seven hollow fiber membrane filter membranes 955 can be disposed parallel to each other, as shown in FIGS. 18 and 20. In one version, the support collar 980 can include a support plate 982 carrying seven open outlet ends 968 extending into the collar 980 for connecting to the filter membranes 955 in a manner similar to that described above regarding FIGS. 16-17. The connection may be achieved by gluing the filter membranes 955 to the open outlet ends 968 with, for example, an epoxy resin, a polyurethane resin, a cyanoacrylate resin, a UV curing acrylic adhesive, or a solvent for the material of the hollow connector 966 such as cyclohexanone. In the version depicted, the stem structure of the open outlet ends 868 of the connector 866 comprises a hollow cylindrical member that fits inside of and is fixed to the filter membranes 955. As such, a diameter of the open outlet ends 968 is substantially similar to or slightly smaller than an inner diameter of the filter membranes 955. In some versions, the filter membranes 955 may be welded to the open outlet ends 968 of the connector 966 by, for example, heat welding (e.g., introducing a hot conical metal tip into the filter membranes 955 to partially melt it), laser welding if the hollow connector 966 is made from a material that absorbs laser radiation, mirror welding, ultrasound welding, and friction welding. Alternately, the filter membranes 955 may be inserted into a mold, and a thermoplastic polymer may be injection-molded around it to form the hollow connector 966. Other designs and configurations for connecting the filter membranes 955 to the open outlet ends 968 are intended to be within the scope of the present disclosure.

Finally, the collar 980 of this embodiment includes a sealing surface 972 that can be received by the stem 156 such that the stem 156 extends therefrom. The stem 156 can be fixed to the sealing surface 972 with adhesive (e.g., a UV curing acrylic adhesive), epoxy, welding, bonding, etc. The stem 156 receives the pharmaceutical fluid after it passes through the pores 162 in the filter membranes 955. From there, the now filtered fluid passes into the bladder 152 in the same manner described above with respect to FIGS. 3-5.

As discussed above, some embodiments of the disclosed systems include a knob 138, as depicted in FIGS. 1-4, that sealably covers the inlet 124 of the stem 104 to maintain sterility until time for filling. Instead of the knob 138, other embodiments can include a split septum or membrane 151 disposed in the stem 104, as depicted in FIGS. 21 and 22. Prior to and possibly after filling, the septum or membrane 151 provides a sterile closure at the inlet 124 of the stem 104 as depicted in FIG. 21. But the septum or membrane 151 can be punctured or opened by a filling port 157 inserted into the stem 104 during the filling process, as illustrated in FIG. 22. Still other embodiments can be constructed differently. For example, FIGS. 23-27 illustrate an alternative version where neither a knob 138 now a septum or membrane 151 is required. Instead, as shown in FIG. 23, the inlet 124 of the stem 104 can be closed or sealed off with a seal 161 such as a heat seal or otherwise. More particularly, FIGS. 23-27 illustrate a filter 165 disposed between an upper stem portion 107a and a lower stem portion 107b. The upper and lower stem portions 107a, 107b can be any medically suitable material, which may be rigid or flexible and suitable for the intended use, and affixed to opposite ends of the filter 165 with an adhesive, by welding, or otherwise, as shown. So configured, prior to filling a product bag (not shown) that is located downstream from the filter 161, the upper stem portion 107a is cut at a location between the seal 161 and the filter 165, as shown in FIG. 24. This exposes the inlet 124 opening to allow for the receipt of a filling nozzle 157, as shown in FIG. 25. Once filling is complete, the lower stem portion 107b is sealed and cut in a manner similar to that described above with previous versions to both seal the downstream chamber to maintain it sterility, and remove the filter 165 for integrity testing.

From the foregoing, it can be seen that various filtering arrangements can serve the principles of the present disclosure including introducing fluid to the product bag in a sterilized manner.

With a medical product 101 arranged as described in FIGS. 1-4, the medical product 101 is initially delivered to a pharmacist with the product concentrate 105 disposed in the chamber 103, 153 of the product bag 100, 150. In this configuration, the product concentrate 105 and the chamber 103 is sterile. In some embodiments, the product concentrate can be introduced into the chamber 103, 153 in a sterile aseptic filling environment, or a product concentrate can be introduced into the chamber 103, 153 and terminally sterilized in a an autoclave or other sterilization facility. In still further versions, a product can be introduced into the chamber 103, 153 and subsequently lyophilized in the product bag 100, 150. Thus, it can be appreciated that in order to reconstitute a product from concentrate, the concentrate and a diluent must be introduced into the chamber 103, 153 and mixed.

The first step for the pharmacist then is to introduce a diluent into the pre-filled sterile chamber 103, 153 through the filtration device 106. As described above with respect to any of FIGS. 1-20, each of the filters, filter membranes, filtration devices, etc., are equipped to sterilize the diluent as the diluent passes therethrough and into the chamber 103, 153. This introduction of the diluent can be achieved either manually, automatically, or semi-automatically. One possible automatic system and process that may be utilized is disclosed in PCT/US17/14264, entitled METHOD AND MACHINE FOR PRODUCING STERILE SOLUTION PRODUCT BAGS, the entire contents of which are incorporated herein. In one version where the stem 156 includes the sealing knob 138 depicted in FIGS. 1-4, this process simply requires removing the knob 138 and introduces a filling port into the stem 156. In other embodiments that include a septum or membrane 151 as depicted in FIGS. 4A, the filing port 155 is simply introduced into the stem to pierce the septum or membrane 151 and begin introducing diluent to the chamber 103, 153.

Then, once the desired amount of diluent is added to the chamber 103, 153, the stem 156 is sealed and cut at the second part 132 of the stem 156 as discussed above regarding FIGS. 1-4. This ensures that the stem 156 is completely sealed. Moreover, this enables the performance of a filter integrity test on the filter. If the filter passes the test, the sterility of the diluent introduced into the chamber 103, 153 is confirmed and the product bag 100, 150 can be agitated or otherwise manipulated to thoroughly reconstitute he product prior to patient administration. If the filter does not pass the test, the diluent and product concentrate may have to be discarded as the sterility may be considered compromised or of lesser than desired sterility.

Referring back to FIGS. 1-4, some embodiments of the medical products 101 within the scope of the present disclosure can also include addition ports 120 connected to the product bags 100, 150. Such addition ports 120 can include ports designed for coupling to a drug vial and introducing a drug or other pharmaceutical fluid from the drug vial to the chamber 103, 153 with the product concentrate 105 either before or after introducing pharmaceutical fluid to the chamber 103, 153 through the provided filtration device 106, 155. The addition port 120 can be a vial adaptor that can take many different forms, but one example is disclosed in U.S. Pat. No. 5,304,163, entitled INTEGRAL RECONSTITUTION DEVICE, the entire contents of which are incorporated herein by reference.

Thus far, only sterile product bags 100, 150 with single chambers 103, 153 have been discussed. But the benefits of the present disclosure can also be realized in sterile product bags with more than a single chamber. As an example, one conventional dual-chamber product bag that can benefit from the technologies disclosed in the present application is disclosed in U.S. Pat. No. 5,577,369, entitled METHOD OF MAKING AND FILLING A MULTI-CHAMBER CONMTAINER, the entire contents of which are incorporated herein by reference.

Figure 28:
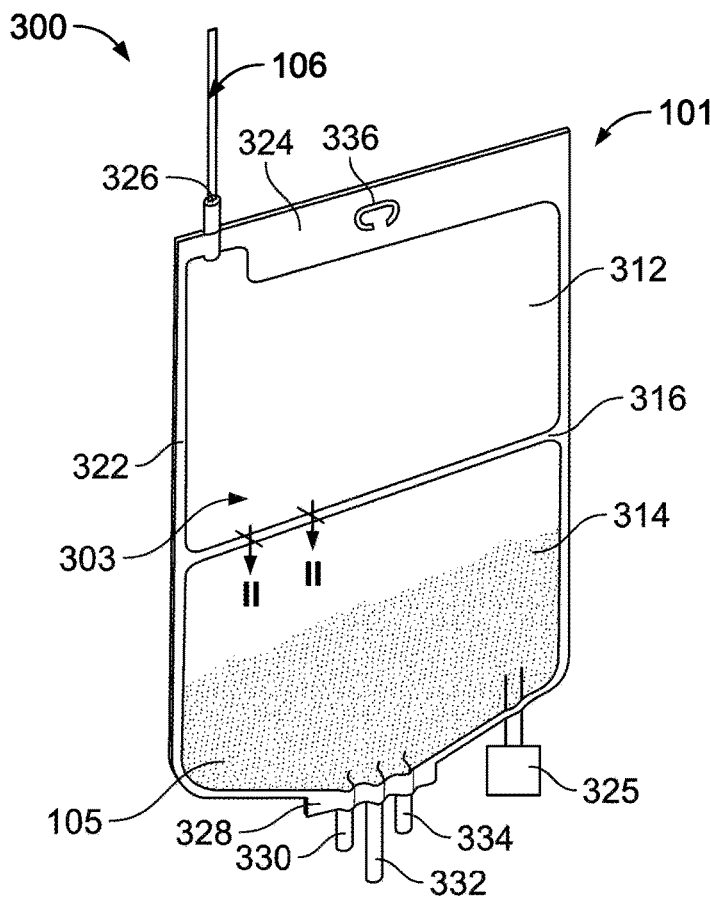
FIG. 28 is a front view of an alternative medical product of the present disclosure having a product bag with two chamber portions.

Referring to FIG. 28, a medical product 101 in accordance with the present disclosure is illustrated including a dual-chambered sterile product bag 300 containing a product concentrate 105. The product bag 300 includes a chamber 303 separated into two chamber portions 312 and 314, the second of which includes the product concentrate 105, for the separate storage of substances and/or solutions. A peelable seal 316 is provided between the chamber portions 312, 314. Although in the embodiment illustrated, the product bag 300 includes two chamber portions 312, 314, it should be appreciated that additional peelable seals may be included to divide the chamber 303 into additional chamber portions.

The product bag 300 is formed from a flexible sheet of plastic. The bag 300 may be formed from two sheets of film that are heat sealed along their edges defining a perimeter seal 305. However, the bag 300 can be formed from a web of film folded over and sealed along three sides. Pursuant to the present invention, the bag 300 can be formed from a multi-layer film discussed below.

Figure 29:
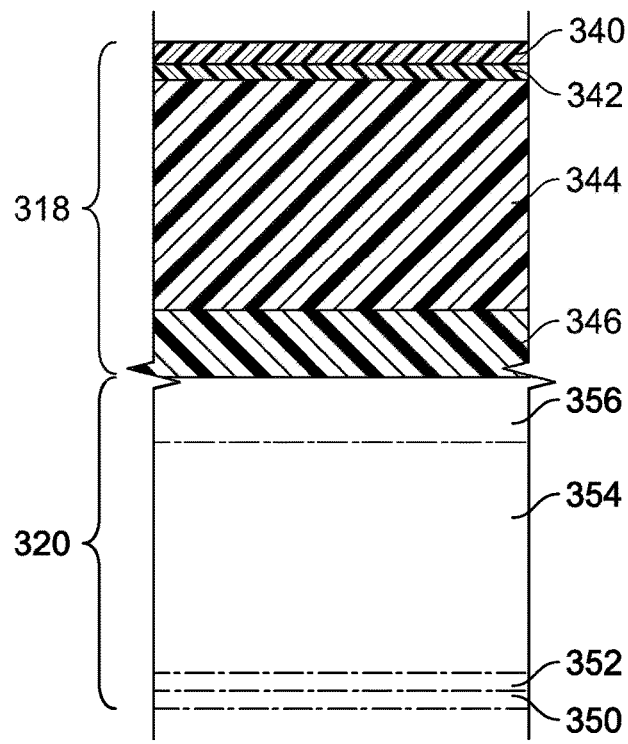
FIG. 29 is a cross-sectional view of an embodiment of a film used to construct the product bag of FIG. 28 taken generally along plane II-II of FIG. 28.

In the illustrated embodiment as shown in FIG. 29, two sheets of film are used. A first or front sheet 318 and a second or rear sheet 320 are sealed about the periphery 322 of the bag 300 by, for example, heat sealing. The peelable seal 316, described more fully below, is provided between the sheets 318, 320 to form the chamber portions 312, 314.

In the preferred embodiment illustrated in FIG. 28, at a top end 324 of the product bag 300 includes a filtration device 106 having a stem 326 equipped with a filter arrangement for sterilizing fluid passing through the stem 326 and into the first chamber portion 312. The filter arrangement can include any of the filters, filters, membranes, and filtration devices described above with respect to FIGS. 1-20. As such, the details will not be repeated.

Still referring to FIG. 28, a bottom end 328 of the product bag 300, in the illustrated embodiment, can potentially include three tubular ports 330, 332, and 334 and an optional vial adaptor 325. More or less than the three tubular ports 330, 332, 334 can be included. The vial adaptor 325 allows the second chamber portion 314 to be filled with a pharmaceutical fluid from a drug vial, as is generally known. As such, the details of the vial adaptor 325 will not be repeated. The tubular ports 330, 332, and 334 can allow the medical substances contained within the product bag 300 to be discharged to one or more patients. Similarly, the tubular ports 330, 332, and 334 can allow medicaments to be injected into the bag 300.

The tubular ports 330, 332, and 334 are mounted in the product bag 300 to communicate with the product bag 300 via the chamber portion 314. The ports 330, 332, and 334 can include a membrane that is pierced by, for example, a cannula or a spike of an administration set for delivery of the contents of the product bag 300 through the administration set to the patient or can also include a Luer-Activated-Device (LAD). Of course, more or less than three ports can be included.

Preferably, at the top end 324 of the product bag 300 is an area which includes a hanger hole 36 for supporting the product bag 300 by, for example, a hook (not shown).

In FIG. 29, the sheets 318, 320 which form the bag 300 are illustrated in cross-sectional view. Specifically, the seal 316 is illustrated at the junction of the sheet 318 with the sheet 320. The seal 316 is formed such that no communication between the chamber portions 312, 314 is provided until the seal 316 is broken. That is, the chamber portions 312, 314 are isolated from each other when the seal 316 is intact such that fluids and gasses cannot pass from one chamber portion to the other. Rupturing or breaking the peelable seal 316 serves to provide communication between the chamber portions 312, 314 allowing a mixing of the substances stored therein.

The sheets 318, 320 are flexible and are preferably made of the same materials. In the illustrated embodiment, the first sheet 318 includes a first layer 340 forming an outer surface or abuse layer of the product bag 300. The first layer 340 may be, for example, a thermoplastic material such as PCCE. A typical thickness of the first layer 340, in a preferred embodiment, is approximately 0.55 mil but may vary, for example, between 0.40 mil and 0.70 mil.

A tie layer 342 can be provided to provide a binding layer between the outside layer 340 and a second layer 344 of the sheet 318 which is RF-responsive. Although in a preferred embodiment, the tie layer 342 has a thickness of approximately 0.4 mils, the tie layer 342 may, however, have a varied thickness, for example, between 0.25 mils and 0.55 mils. The tie layer 342 can be a thermoplastic material such as ethyl vinyl acetate (EVA) modified with malic anhydride.

The second layer 344 is an RF-responsive layer that, as discussed below, cooperates with a sealing or inner layer 346 to create the seal. The second layer 344 can be any RF-responsive material. In a preferred embodiment, the RF-responsive material is an ethyl vinyl acetate (EVA). It has been found that a layer thickness of approximately 6.2 mils functions satisfactorily. However, the second layer 344 can have a varied thickness of between, for example, at least 5.75 mils and 6.75 mils.

The sealing layer 346 is made of a non-RF responsive material. Preferably, the non-RF responsive layer includes at least two materials having different melting points. In an embodiment, the non-RF-responsive layer is an alloy of styrene-ethylene-butyl-styrene (SEBS) for example, Kraton®, and ethylene polypropylene copolymer. It has been found that if the sealing layer has a thickness of approximately 1.6 mils it functions satisfactorily. However, the thickness may vary, for example, between 1.40 mils and 1.80 mils.

The sealing layer 346 is adjacent the solution side of the container such that when the seal 316 is ruptured, communication is provided between the chamber portions 312, 314. As noted above, the four-layer film illustrated in FIG. 29 has at least one RF-responsive layer 344 and one non-RF responsive layer 346. A RF field heats a seal bar 62 (not shown) which heats the RF-responsive layer 344 which, in turn, heats the non-RF responsive layer 346 to soften the layer 346, but not liquify same. A resulting cohesive bond develops from contact between the non-RF responsive layer 346 of the sheet 318 and a corresponding non-RF responsive layer 456 of the sheet 320, but fusion between the layers, which can cause permanent bonding, does not occur.

As previously indicated, the product bag 300 can be formed by folding a single web, such as the sheet 318, or alternatively, the sheet 320 can be further provided in addition to the sheet 318. In the preferred embodiment, the sheet 320 is a four-layer film in which layers 50, 52, 54 and 56 of the sheet 320 substantially correspond to the layers 40, 42, 44 and 46 of the sheet 318, respectively. As a result, the sealing layer 456 of the sheet 320 forms a cohesive bond with the sealing layer 346 of the sheet 318. The cohesive bond formed is the peelable seal 316.

It should be appreciated that fewer layers for each of the sheets 318, 320 than the four-layer film described with reference to FIG. 29 can be used to create the peelable seal 316 of the present invention. Two layers can be used, one layer being RF-responsive and the other layer being non-RF responsive. Reliability and strengthening of the peelable seal 316 may be further enhanced by using corona treatment or an extrusion process.

The peelable seal 316 is preferably formed to withstand external pressure to one or both chamber portions 312, 314 of the container. Furthermore, the peelable seal 316 is capable of withstanding pressure exerted by dropping the product bag 300 either on its side or if it is dropped flat. Preferably, the peelable seal 316 can withstand rupture from a drop of up to six feet.

Post-sterilization of the chamber portions 312, 314 of the product bag 300 substantially increases the pressure which the peelable seal 316 is capable of withstanding before rupture. More specifically, sterilization can increase seal strength between 40 and 80 percent.

During use, the product bag 300 can be supplied to a pharmacist with the first chamber portion 312 empty but the second chamber portion 314 pre-filled with a concentrate requiring reconstitution. The concentrate may be in the form of powder, gel, foam, liquid, flakes, etc.

To perform reconstitution when the first chamber 312 is completely empty and the second chamber 314 contains the pre-filled sterile product concentrate 105, the pharmacist can introduce a diluent to the first camber portion 312 through the filtered stem 326 in a manner same as that described above with reference to the product bags 100, 150 in FIGS. 1-20. Subsequently, the filtered stem 326 can be sealed, cut, and integrity tested. If the filter passes the integrity test, the pharmacist can determine that the diluent in the first chamber portion 312 is sufficiently sterile to continue. Next, a user can apply a compressive force to the outside of the product bag 300 in the region of the first chamber portion 312, which creates a hydraulic force applied to the peel seal 316 ultimately breaking the peel seal 316 and causing fluid communication between the first and second chamber portions 312, 314. Continued manual manipulation of the product bag 300 mixes the concentrate 105 and diluent thoroughly to arrive at a solution ready for patient administration.

Figure 30:
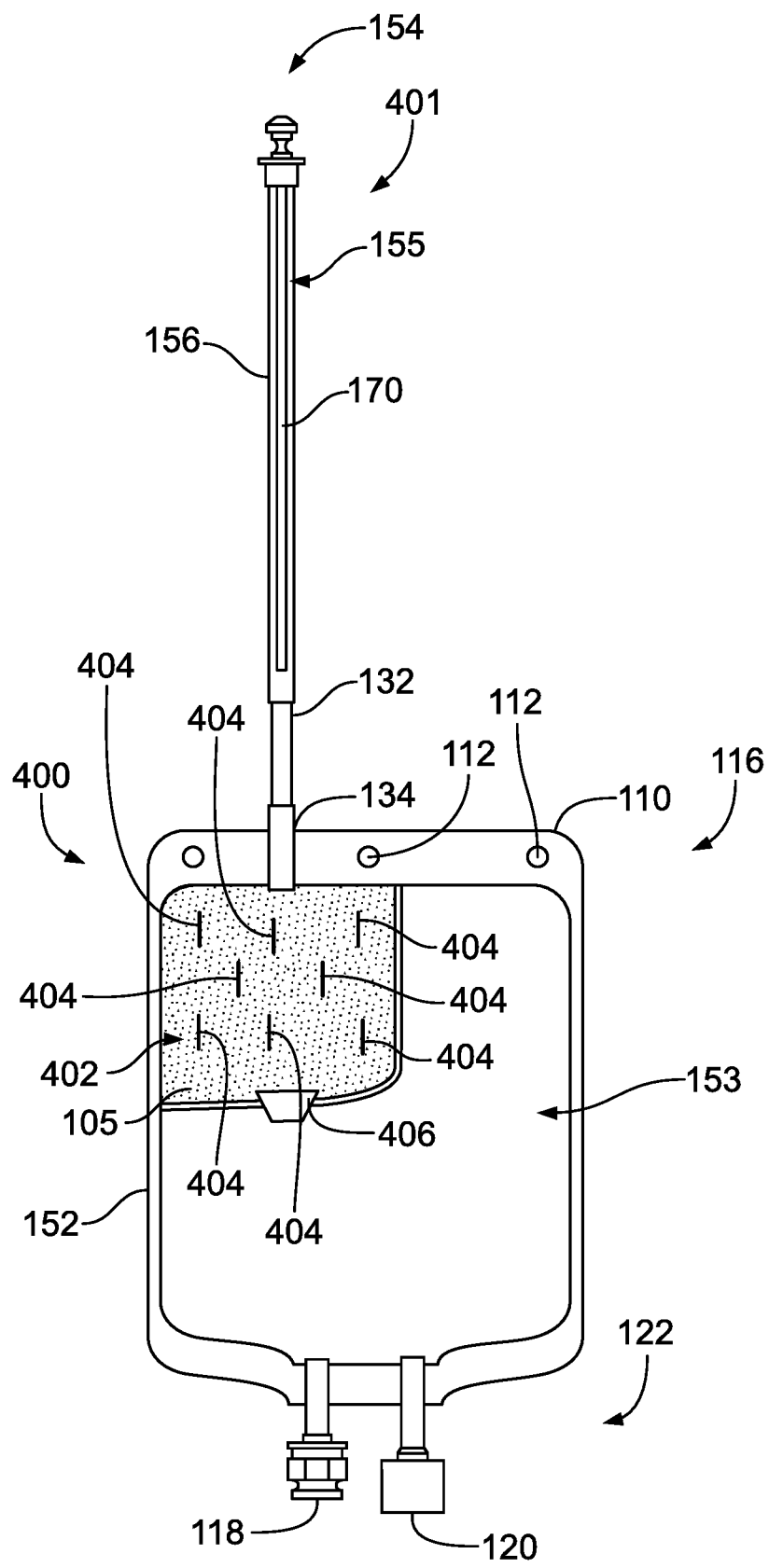
FIG. 30 is a front view of another alternative medical product of the present disclosure having a product bag with two chamber portions.

While the medical product 101 described with reference to FIGS. 28 and 29 includes a relatively conventional dual chamber with peel seal construct, the present disclosure also includes non-conventional dual chamber type product bags. For example, FIG. 30 depicts an alternative medical product 401 including dual chamber product bag 400 that is very similar to the product bag 150 described above with reference to FIGS. 3 and 4. As such, for the sake of simplicity, many of the same reference numerals are used in FIG. 30 as used in FIGS. 3 and 4. New or different features are represented with different reference numbers. Most specifically, the product bag 400 in FIG. 30 includes a bladder 152 defining a sterile chamber 153 same as that in FIGS. 3 and 4. Additionally, however, the bladder 152 defines a concentrate storage chamber 402 in which a concentrate 105 resides prior to mixing with a diluent or other medical fluid. As depicted, the concentrate storage chamber 402 is a subdivided region of the sterile chamber 153 as a whole and resides in direct communication with the duct 134 that is coupled to the stem 156 and filtration device 155. So configured, to reconstitute the concentrate stored in the concentrate storage chamber 402, a diluent can be supplied to the concentrate storage chamber 402 via the filtration device 155 in a manner identical to those manners described above with respect to FIGS. 1-4, for example. As the diluent enters the concentrate storage chamber 402, it immediately contacts the concentrate 105 and begins mixing. In the version of the product bag 400 depicted in FIG. 30, the concentrate storage chamber 402 also includes a plurality of vertical button seals 404, where the two membranes or films defining the front and rear sides of the bladder 102 are bonded together by welds, adhesive, or otherwise. These button seals 404 can facilitate the mixing process by creating a tortuous and divided fluid flow path for the diluent as it moves through the concentrate storage chamber 402 and mixes with the concentrate 105. While vertical button seals 404 are illustrated, the seals 404 can take generally any form or shape including horizontal seals, wedge shaped seals, V-shaped or upside down V-shaped seals, or otherwise. Finally, as shown, the concentrate storage chamber 402 includes a one-way valve 406, which upon exposure to a predetermined amount of pressure in the concentrate storage chamber 402 opens to allow flow of the reconstituted product from the concentrate storage chamber 402 to the sterile chamber 153. In some embodiments, the one-way valve 406 can be a planar one-way film valve, a duck bill valve, or other suitable type of valve that allows flow out of but not back into the concentrate storage chamber 402. In other embodiments, instead of the one-way valve 406, the product bag 400 can include a peel seal at the interface between the concentrate storage chamber 402 and the larger sterile chamber 153 such that during mixing of the concentrate 105 in the concentrate storage chamber 402 hydraulic pressures in the concentrate storage chamber 402 can break the seal and allow the reconstituted product to freely flow out of the concentrate storage chamber 402.

While the product bag 400 in FIG. 30 includes a single concentrate storage chamber 402 in communication with a single stem 156 and filtration device, alternative versions can have two or more concentrate storage chambers. For example, in one alternative, the product bag 400 can include two concentrate storage chambers 402 located in series such that a second concentrate storage chamber is located immediately below the concentrate storage chamber 402 depicted in FIG. 30 and opposite the stem 156 and filtration device 155. In such a design, both of the concentrate storage chambers could contain same or different concentrates intended to be mixed together during and/or upon reconstitution. Similar valving and/or peel seal arrangements could exist between the two concentrate storage chambers to control flow. In yet another embodiment, the product bag 400 in FIG. 30 could include two or more side-by-side concentrate storage chambers, each associated with its own stem 156 and filtration device 155 such that fluids could be simultaneously delivered to all concentrate storage chambers, which may contain same or different concentrates. Then, upon reconstitution in each of the concentrate storage chambers, the two reconstituted products could be mixed in the larger sterile chamber 153. Such configurations may facilitate multi-stage mixing and reconstitution processes, for example. In still further embodiments, the administration port 118 of the product bag 400 in FIG. 30 can be fluidly connected to a static mixing device to further mix the various ingredients initially mixed in the concentrate storage chamber(s) and/or sterile product chamber 153. Finally, while the concentrate storage chamber 402, stem 156 and filtration device 155 in FIG. 30 are positioned at the top of the product bag 400 relative to the orientation of FIG. 30, in other embodiments the relative positioning of these components can vary. For example, in one version, the concentrate storage chamber 402, stem 156, and filtration device 155 can be located along a side wall and toward the bottom of the bag 400 depicted in FIG. 30. Other variations are possible.

Throughout the foregoing disclosure, the various product bags 100, 150, 300 have been described as optionally including an addition port 120, 330,332, 334 for facilitating the introduction of product concentrate into the bag for reconstitution. Other embodiments of the addition ports can also include the Luer-Activate-Device (LAD) (also commonly be referred to as a Luer-Activated-Valve (LAV)) attached to the bag and in fluid communication with the bladder to provide multiple resealable connections to the interior of the bladder. The LAD could be used to introduce medical fluids such as a product concentrate to the bag similar to the vial adaptor described above. This LAD could be included instead of a vial adaptor, for example 325, or in addition to a vial adaptor. In one version of the disclosure where the product bag includes a LAD, the LAD can also be used to not only provide a resealable connection to the interior of the bag for adding substances to the bag but also provide a resealable connection to the interior to selectively withdraw multiple distinct doses from the bag, after the bag has been filled with a medical fluid such as a medicament or nutritional substance. The LAD can also be used as an embodiment of an administration port 118.

Furthermore, while the foregoing disclosure only specifically describes embodiments of product bags with one filter arrangement disposed, for example, in line with a stem as described with reference to FIGS. 1-20, other embodiments of product bags constructed in accordance with the present disclosure can include a plurality of separate filters in communication with the chamber of the product bag. For example, in one alternative embodiment, the product bag 150 in FIGS. 3 and 4 can include two or more stems 156 communicating with the chamber 153, each stem containing a separate in-line filter 155. So configured, it may be possible to mix or combine a plurality of medical fluids or ingredients in the product bag by introducing those fluids or ingredients through the plurality of filters 155, either simultaneously or in sequence. Having a plurality of distinct filters 155 may also be beneficial for increasing the rate of filling a product bag with a single medical by simply introducing fluid through two filters simultaneously as opposed to being limited to only a single filter or where two of the ingredients are not compatible in concentrated form but are compatible once diluted. Having separate distinct stems removes the opportunity for contact in the concentrated forms. Moreover, the addition of two fluids through distinct stems reduces the need for the addition of the two fluids to be close in time. Because the medications are sterile filtered after the point of connection to the stem, the addition steps may not need to be performed within a hood or other asceptic environment. Such an arrangement may also be beneficial in specific versions where any one of the product bags 100, 150, 300, 400 described herein is further equipped with a LAD, as mentioned above. That is, in some versions, the product bag equipped with a LAD can be filled with a compounded or reconstituted medicament or fluid through the filter(s) and a pharmacist, for example, may withdraw a plurality of doses of the same medicament or fluid for different patients, where those doses may or may not be different for each patient.

While certain representative versions of the claimed subject matter have been described herein for purposes of illustrating the invention, it will be apparent to those skilled in the art that various changes in the devices and methods disclosed may be made without departing from the spirit and scope of the invention, which is defined by the following claims and is not limited in any manner by the foregoing description.

The invention claimed is:

1. A medical product comprising:
   a bladder having a perimeter seal and defining a sterile chamber;
   a filtration device comprising:
     a connector having an open outlet end;
     a stem extending through the perimeter seal and having an inlet end accessible from outside of the perimeter seal and an outlet end in fluid communication with the sterile chamber; and
     a filter membrane disposed in line with the stem and having a nominal pore size in a range of approximately 0.1 µm to approximately 0.5 µm, the filter membrane is having a hollow core with a wall extending around the hollow core, an open first end, a closed second end, and pores residing in the wall, wherein the filter membrane is coupled to the connector with the open outlet end of the connector received within filter membrane through the open first end; and
   a sterile product concentrate disposed in the sterile chamber.

2. The medical product of claim 1, wherein the product concentrate comprises a medicinal or nutritional concentrate.

3. The medical product of claim 1, wherein the filter membrane is disposed inside of the stem between the inlet and outlet ends.

4. The medical product of claim 1, wherein the filter membrane has a nominal pore size in a range of approximately 0.1 µm to approximately 0.22 µm.

5. The medical product of claim 1, wherein the chamber comprises at least a first chamber portion in fluid communication with the stem, and a second chamber portion isolated from the first chamber portion by an intermediate seal.

6. The medical product of claim 5, wherein the product concentrate is disposed in the second chamber portion.

7. The medical product of claim 5, wherein the bladder comprises adjacent front and rear films secured together by the perimeter seal, and the intermediate seal comprises a peelable seal formed by a bond between adjacent interior surface portions of the front and rear films, the peelable seal adapted to be broken to facilitate fluid communication between the first and second chamber portions.

8. The medical product of claim 1, wherein the sterile chamber comprises a subdivided concentrate storage chamber in which the concentrate resides, the concentrate storage chamber in direct fluid communication with the stem.

9. A medical product comprising:
   a bladder comprising adjacent front and rear films secured together by a perimeter seal and defining a sterile chamber comprising at least a first chamber portion and a second chamber portion isolated from the first chamber portion by a peelable seal formed by a bond between adjacent interior surface portions of the front and rear films,
   the peelable seal adapted to be broken to facilitate fluid communication between the first and second chamber portions;
   the second chamber portion comprising bonded portions between the front and rear films to facilitate fluid mixing within the second chamber;
   a filtration device comprising a stem and a filter membrane disposed in line with the stem, the stem extending through the perimeter seal and having an inlet end accessible from outside of the perimeter seal and an outlet end in fluid communication with the sterile chamber, the filter membrane with a nominal pore size in a range of approximately 0.1 µm to approximately 0.5 µm, wherein the filter membrane has a hollow core with a wall extending around the hollow core and pores residing in the wall; and
   a sterile product concentrate disposed in the second chamber portion.

10. The medical product of claim 9, wherein the product concentrate comprises a medicinal or nutritional concentrate.

11. The medical product of claim 9, wherein the filter membrane is disposed inside of the stem between the inlet and outlet ends.

12. The medical product of claim 9, wherein the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

13. The medical product of claim 9, wherein the stem is made of at least one of the following materials: PVC, PET, a poly(meth)acrylate, a polycarbonate, a polyolefin, a cycloolefin copolymer, polystyrene, or a silicone polymer.

14. The medical product of claim 9, wherein the filtration device comprises a plurality of parallel filter membranes having hollow cores secured in a side-by-side configuration.

15. A method of reconstituting a product from concentrate, the method comprising:
Providing a bladder having a perimeter seal and defining a sterile chamber containing a sterile product concentrate, at least one filtration device comprising a connector, a stem, and a filter membrane, the stem extending through the perimeter seal and having an inlet end accessible from outside of the perimeter seal and an outlet end in fluid communication with the chamber, the filter membrane with a nominal pore size in a range of approximately 0.1 µm to approximately 0.5 µm, wherein the filter membrane has a hollow core with a wall extending around the hollow core, an open first end, a closed second end, and pores residing in the wall of the fiber;
introducing a pharmaceutical fluid into the filter membrane through an open outlet end of the connection received within the filter membrane received through the open first end and subsequently into the chamber of the bladder through the filter membrane; and
mixing the pharmaceutical fluid and the product concentrate together in the chamber of the bladder to reconstitute the product.

16. The method of claim 15, wherein introducing the pharmaceutical fluid into the chamber of the bladder through the filter membrane comprises introducing the pharmaceutical fluid through a plurality of filter membranes.

17. The method of claim 15, further comprising sealing the bladder and removing the filter membrane from the bladder after introducing the pharmaceutical fluid through the filter membrane.

18. The method of claim 17, wherein sealing the bladder and removing the filter membrane comprises sealing a portion of the stem of the filtration device to form a seal located between the bladder and the filter membrane and cutting the stem adjacent to the seal.

19. The method of claim 17, further comprising performing a filter integrity test on the filter membrane after removing the filter membrane from of the product bag.

20. The method of claim 19, wherein performing the filter integrity test comprises one of a pressure degradation test, a bubble point test, a water intrusion test, or a water flow test.

21. The method of claim 15, wherein providing at least one filtration device comprises providing a plurality of separate and distinct filtrations devices such that introducing a pharmaceutical fluid into the chamber of the bladder through the filter membrane comprises introducing at least one pharmaceutical fluid into the chamber of the bladder through the plurality of filtration devices.

* * * * *

UNITED STATES PATENT AND TRADEMARK OFFICE
CERTIFICATE OF CORRECTION

| | | |
|---|---|---|
| PATENT NO. | : 11,974,966 B2 | Page 1 of 1 |
| APPLICATION NO. | : 16/631030 | |
| DATED | : May 7, 2024 | |
| INVENTOR(S) | : Schuck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1147 days.

Signed and Sealed this
Twenty-ninth Day of April, 2025

Coke Morgan Stewart
*Acting Director of the United States Patent and Trademark Office*